(12) United States Patent
Perkins et al.

(10) Patent No.: US 9,198,779 B2
(45) Date of Patent: *Dec. 1, 2015

(54) LEVER-ACTUATED DEVICE FOR EXTERNAL PROSTHESIS

(71) Applicant: COYOTE DESIGN AND MANUFACTURING, INC., Boise, ID (US)

(72) Inventors: Matt Perkins, Boise, ID (US); Travis Dean, Boise, ID (US)

(73) Assignee: COYOTE DESIGN AND MANUFACTURING, INC., Boise, ID (US)

( * ) Notice: Subject to any disclaimer, the term of this patent is extended or adjusted under 35 U.S.C. 154(b) by 129 days.

This patent is subject to a terminal disclaimer.

(21) Appl. No.: 13/654,667

(22) Filed: Oct. 18, 2012

(65) Prior Publication Data

US 2013/0282143 A1    Oct. 24, 2013

Related U.S. Application Data

(63) Continuation-in-part of application No. 13/104,937, filed on May 10, 2011, now Pat. No. 8,562,692.

(60) Provisional application No. 61/549,190, filed on Oct. 19, 2011, provisional application No. 61/333,167, filed on May 10, 2010.

(51) Int. Cl.
   *A61F 2/78*    (2006.01)
   *A61F 2/80*    (2006.01)

(52) U.S. Cl.
   CPC ............... *A61F 2/7812* (2013.01); *A61F 2/80* (2013.01); *A61F 2002/7875* (2013.01); *A61F 2002/802* (2013.01); *A61F 2002/805* (2013.01)

(58) Field of Classification Search
   CPC ................................. A61F 2002/7825
   USPC ..................................... 623/33–37
   See application file for complete search history.

(56) References Cited

U.S. PATENT DOCUMENTS

1,586,015 A    5/1926    Underwood
2,530,285 A    11/1950   Catranis (Continued)

FOREIGN PATENT DOCUMENTS

DE    102005034388 A1    12/2006

OTHER PUBLICATIONS

Translation of German Patent DE10 2005 034 388 A1, published on Dec. 28, 2006.

*Primary Examiner* — David H Willse
(74) *Attorney, Agent, or Firm* — Pedersen and Company, PLLC; Ken J. Pedersen; Barbara S. Pedersen

(57) ABSTRACT

A lever-actuated distal lock connects a limb liner to a prosthetic leg or arm hard socket. In some versions, air-sealing capability may limit/prevent air flow through the distal lock, even with vacuum inside the socket. To unlatch the lock, a lever is swung to pull a sliding shaft outward in the lock housing. Swung in the opposite direction, the lever releases the sliding shaft to be biased to a latched position wherein slanted surfaces of the shaft inner end and a liner pin cooperate to allow the pin to slide down into, but not up out of, the lock. In some versions, the shaft inner end slides relative to, but is biased away from, the shaft opposite end, so that the inner end moves out of the way of the downwardly-sliding pin, without moving the entire lock shaft and without disrupting the optional air seal.

26 Claims, 16 Drawing Sheets

(56) References Cited

U.S. PATENT DOCUMENTS

| | | | |
|---|---|---|---|
| 2,533,404 | A | 12/1950 | Sharp et al. |
| 2,569,790 | A | 10/1951 | White et al. |
| 2,790,180 | A | 4/1957 | Hauser |
| 2,897,512 | A | 8/1959 | Sackett |
| 4,634,446 | A | 1/1987 | Kristinsson |
| 5,007,937 | A | 4/1991 | Fishman et al. |
| 5,201,774 | A | 4/1993 | Greene |
| 5,376,131 | A | 12/1994 | Lenze et al. |
| 5,507,834 | A | 4/1996 | Laghi |
| 5,507,837 | A | 4/1996 | Laghi |
| 5,658,353 | A | 8/1997 | Layton |
| 5,709,017 | A | 1/1998 | Hill |
| 5,888,215 | A | 3/1999 | Roos et al. |
| 5,888,234 | A | 3/1999 | Littig |
| 5,904,722 | A | 5/1999 | Caspers |
| 6,106,559 | A | 8/2000 | Meyer |
| 6,334,876 | B1 | 1/2002 | Perkins |
| 6,361,569 | B1 * | 3/2002 | Slemker et al. ............ 623/33 |
| 6,626,952 | B2 | 9/2003 | Janusson et al. |
| 6,706,364 | B2 | 3/2004 | Janusson et al. |
| 7,427,298 | B1 | 9/2008 | Swanson |
| 7,993,413 | B2 | 8/2011 | Perkins et al. |
| 8,343,233 | B2 | 1/2013 | Perkins et al. |

* cited by examiner

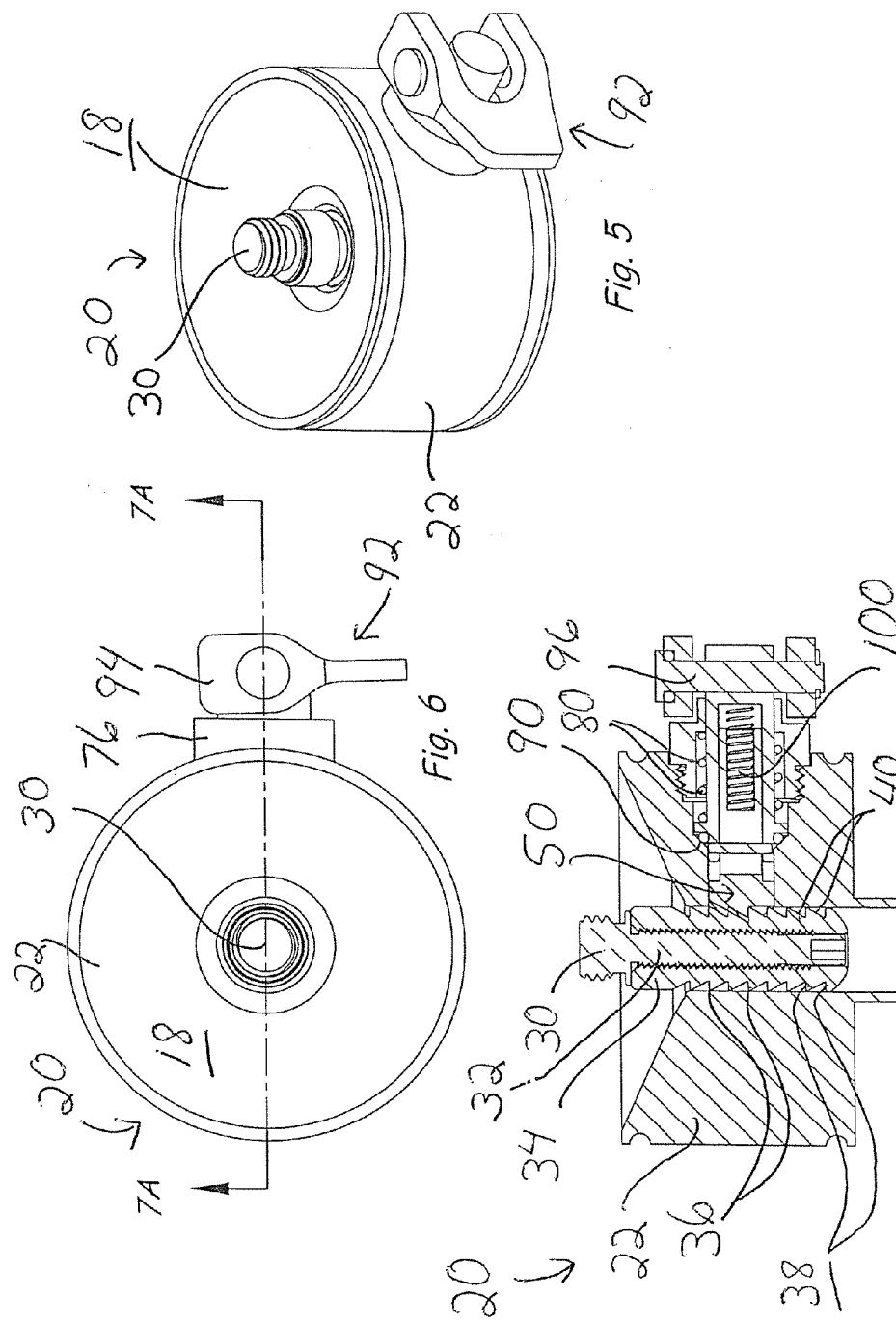

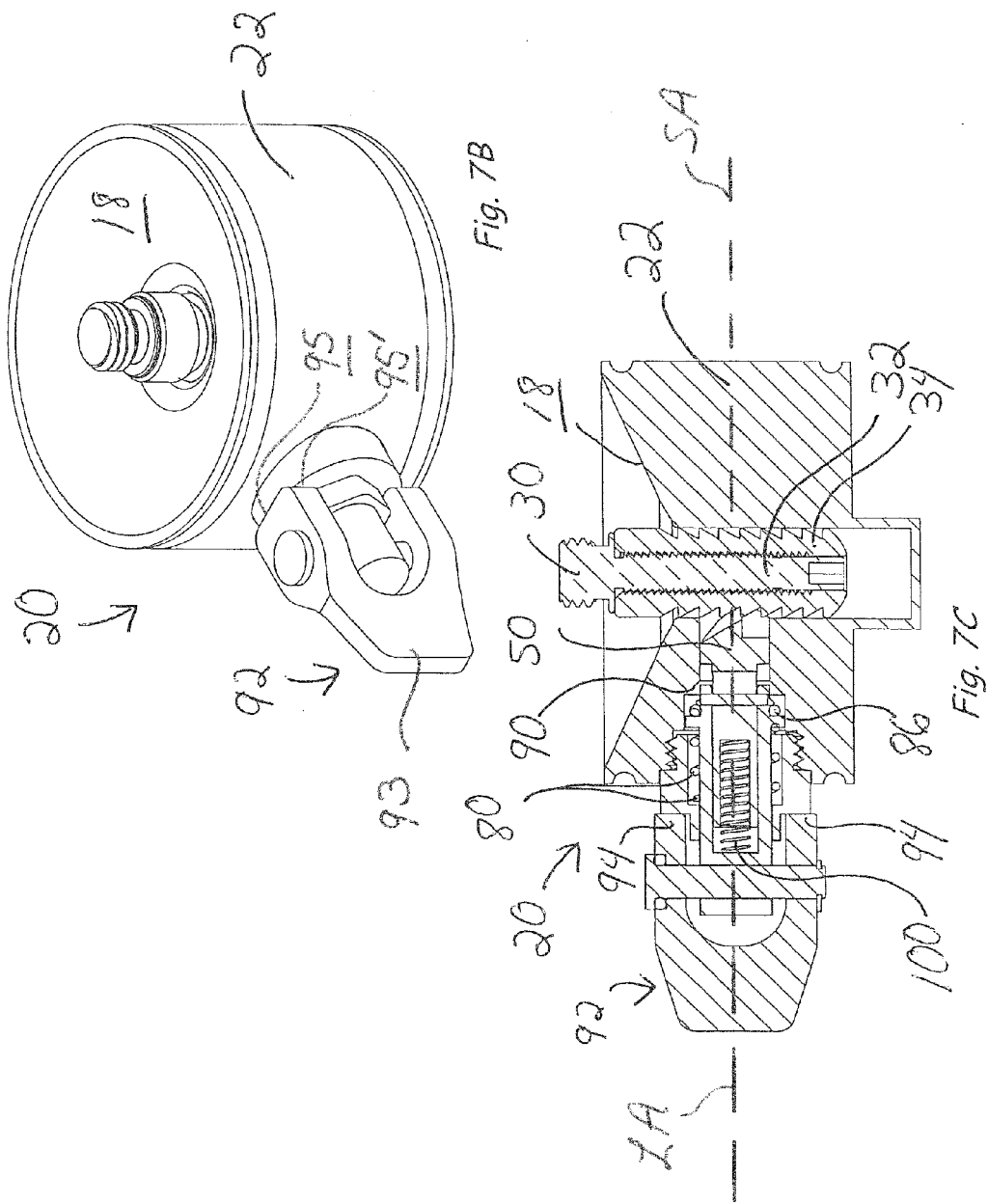

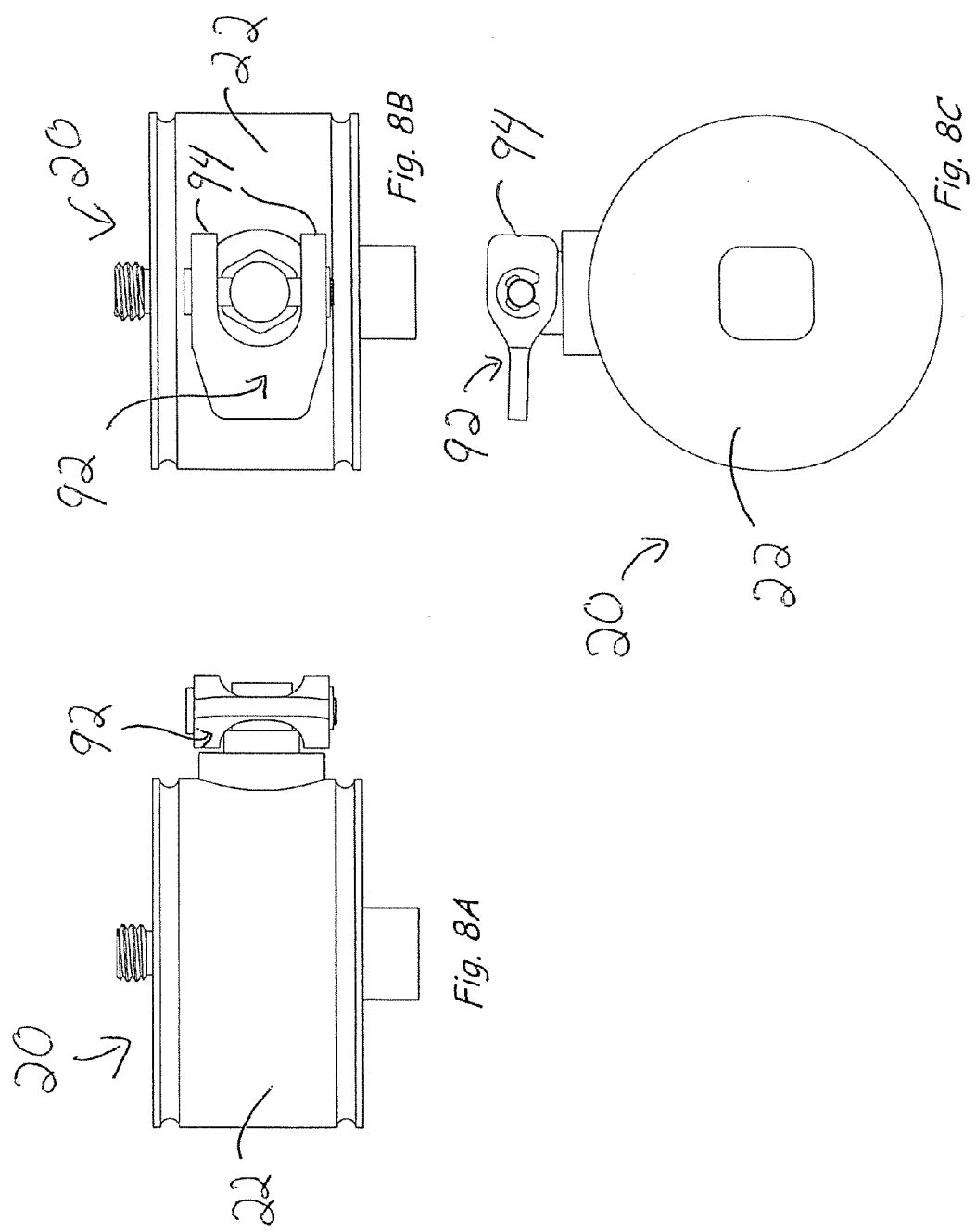

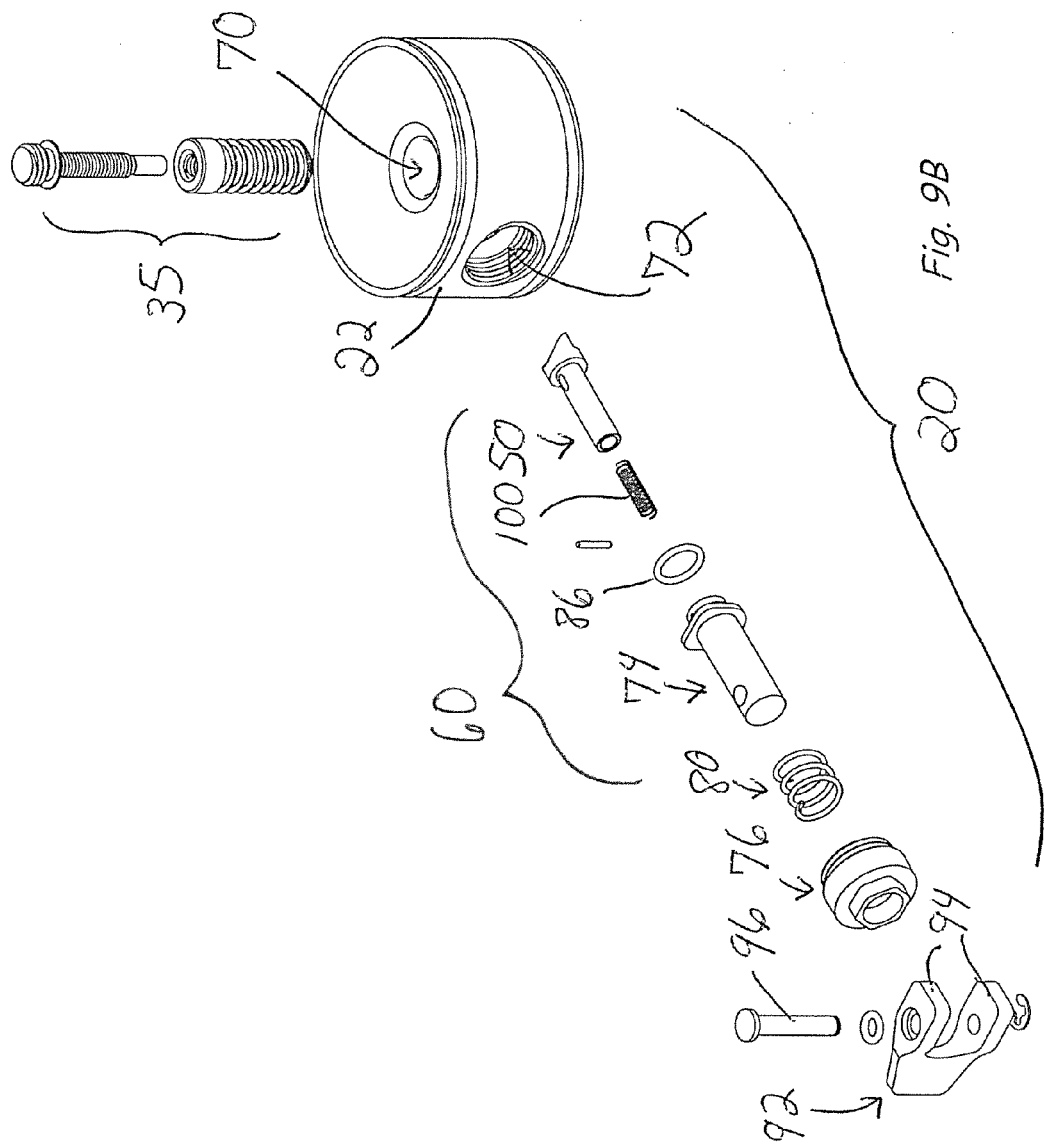

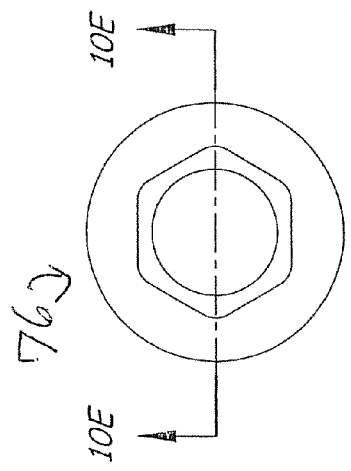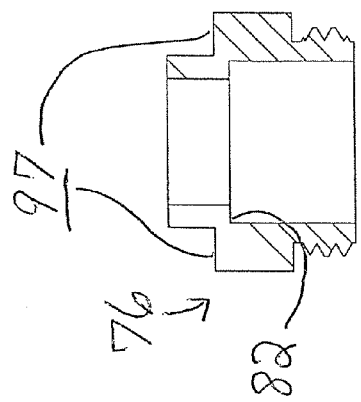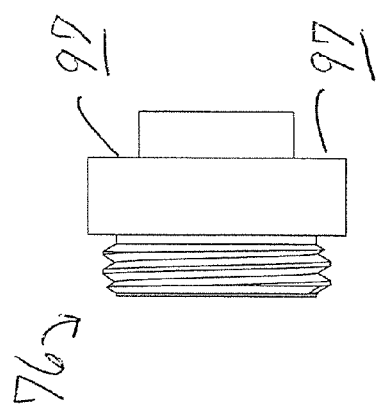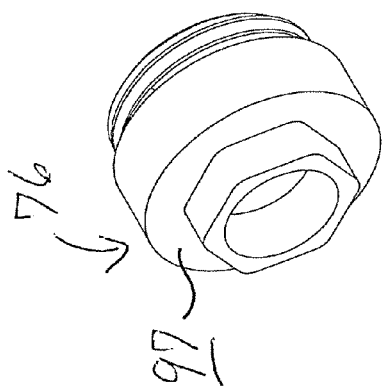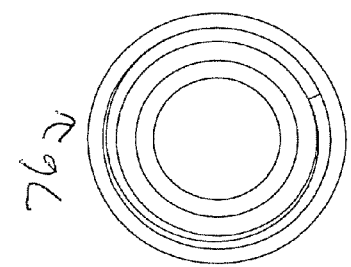

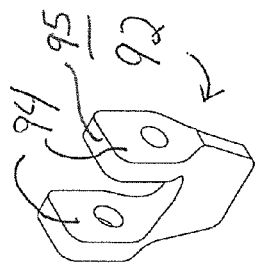
Fig. 11A
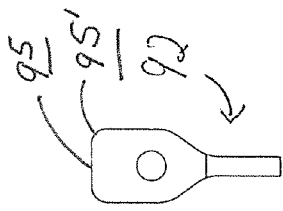
Fig. 11C
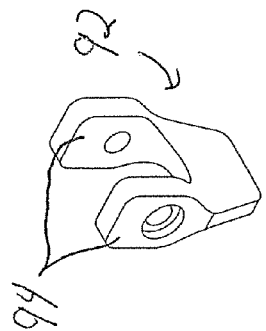
Fig. 11B
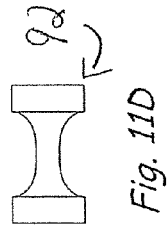
Fig. 11D
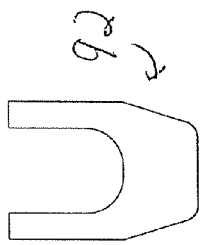
Fig. 11E
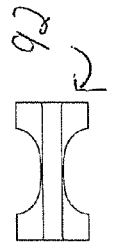
Fig. 11F
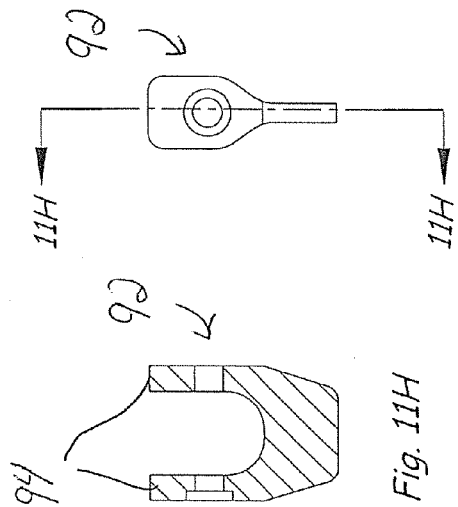
Fig. 11G
Fig. 11H

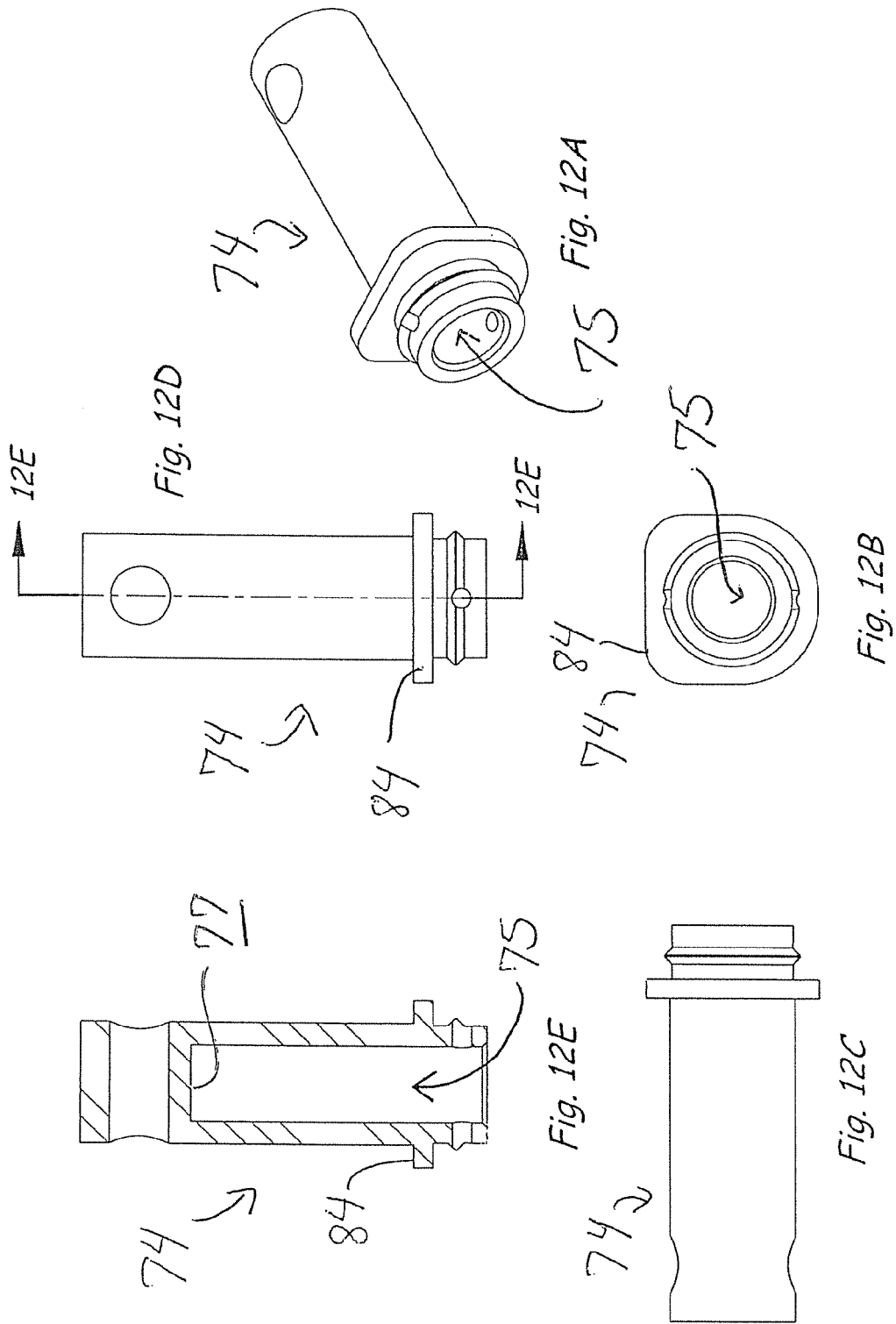

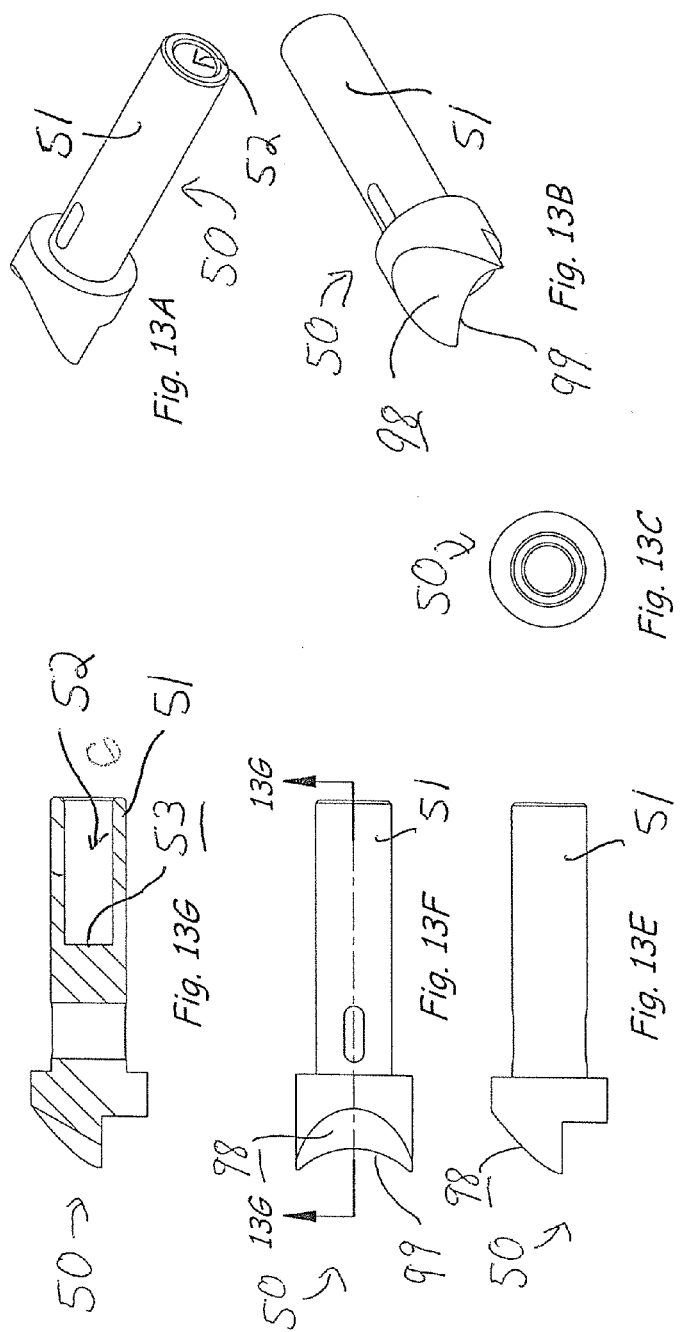

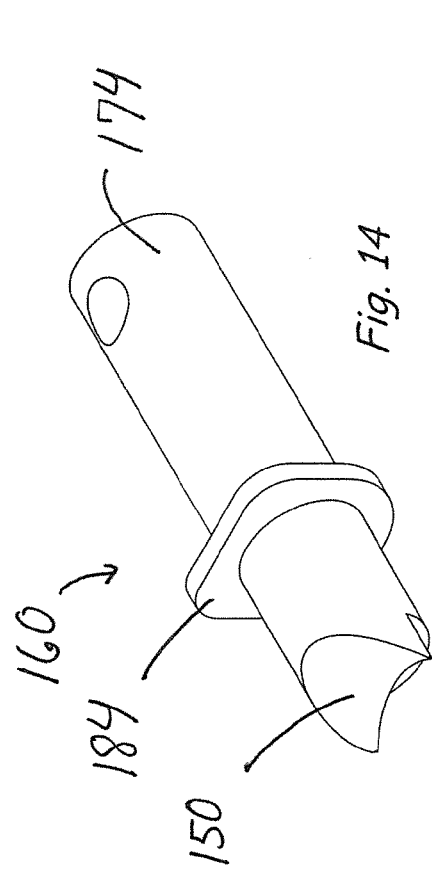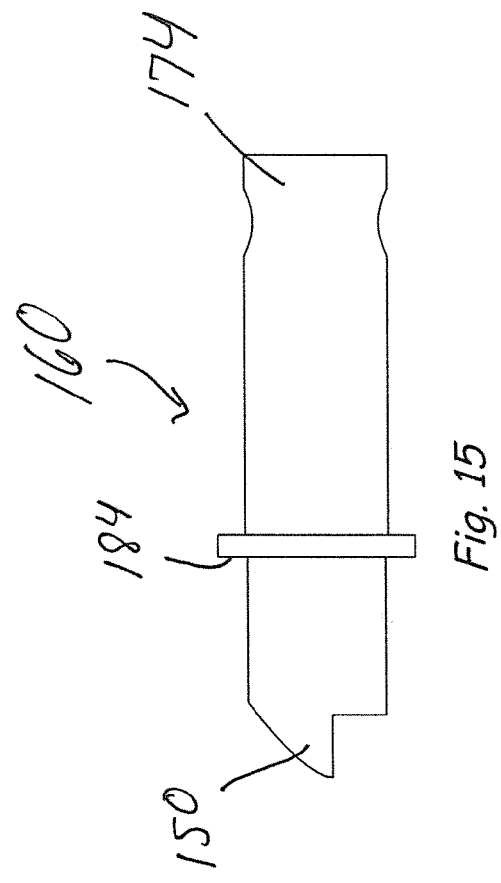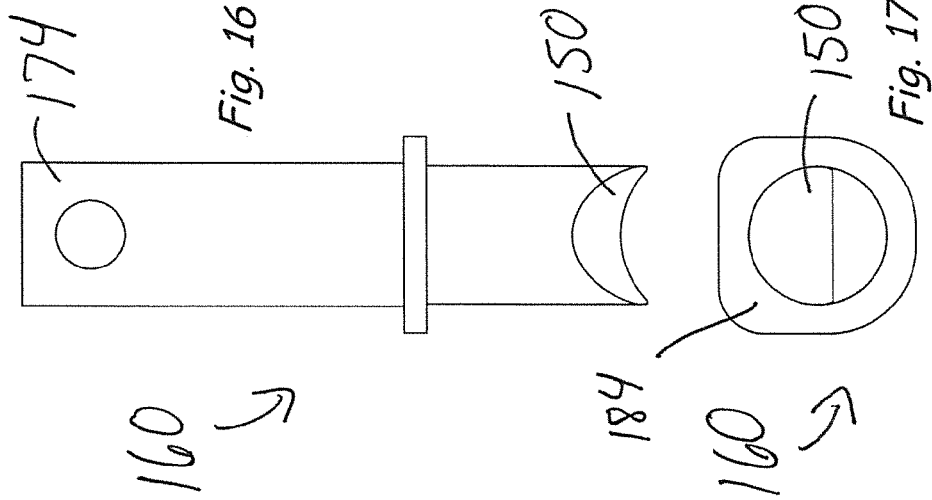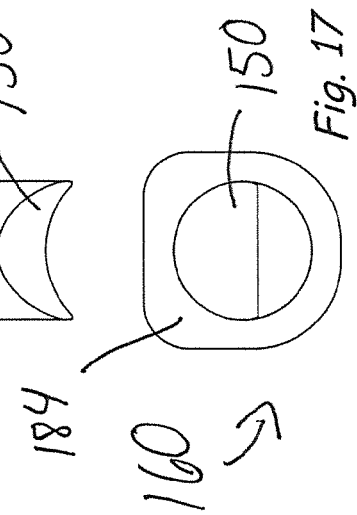

LEVER-ACTUATED DEVICE FOR EXTERNAL PROSTHESIS

This application claims benefit of Provisional Application Ser. No. 61/549,190, filed Oct. 19, 2011, and is a continuation-in-part of Non-Provisional application Ser. No. 13/104,937, filed May 10, 2011, and issued on Oct. 22, 2013 as U.S. Pat. No. 8,562,692, which claims benefit of Provisional Application Ser. No. 61/333,167, filed May 10, 2010, the disclosures of which are both incorporated herein by this reference.

BACKGROUND OF THE INVENTION

1. Field of the Invention

The present invention relates to lever-operated mechanisms for external prostheses. Certain embodiments relate to lever-operated mechanisms for a prosthetic system comprising a hard socket, for example, for a leg or arm prosthesis. Said lever-operated mechanisms may be used as a fastening mechanism to connect a hard socket to a liner for a residual limb, and/or as an air valve or other air-control passageway that is manually opened and closed, and/or other mechanisms that require a latch.

The preferred lever-operated mechanism is a lock system for connecting the distal end of a limb liner to the distal end of a hard socket. The lock is actuated by a lever system provided at or near the outer surface of the hard socket, wherein the lever may be easily swung to open and close the lock. When in the latched configuration, the preferred lock mechanism locks a liner pin into a bore in the hard socket, wherein the liner pin is an elongated pin assembly that protrudes downward from the distal end of the liner on the wearer's residual leg. When the wearer unlatches the preferred lock mechanism, with an easy and comfortable swing of the latch handle, the liner pin, and therefore, the liner and residual limb, are removable from the socket. Certain embodiments further have pressure-control features, such as adaptations for maintaining vacuum established inside the well of a hard socket in some suspension systems.

2. Related Art

Optimum connection/suspension methods for securing a prosthetic limb to a residual limb take into account several factors, including control, comfort, ease of donning and removal, and long term effects on the health of the skin and other tissue. These factors are weighed differently and influenced differently, depending on the wearer's residual limb, level of activity, and preferences. One reason that suspension solutions are not simple is that gravitational and other forces tend to cause separation between a prosthetic limb and a residual limb. This happens especially during the swing phase of the gait, when a prosthetic leg is additionally subjected to centrifugal forces. Patients have routinely worn a variety of belts, straps, cuffs and harnesses to prevent the prosthetic limb from separating from the residual limb, but such devices are inconvenient and tend to cause chafing against the patient's body, giving rise to sores and abrasions.

Advanced methods of suspension have been developed in recent years, for example distal lock mechanisms, proximal attachment systems, and "suction" and "vacuum" suspension. Examples of proximal attachment systems are those developed by the instant inventor(s) (Perkins, Coyote Design and Manufacturing, Inc., Boise, Ill., USA), illustrated in U.S. Pat. Nos. 6,666,894; 7,077,868; 7,431,738; and 7,850,739. Examples of distal locks are those developed by the instant inventor(s), illustrated in U.S. Pat. No. 6,334,876 ("876"), issued Jan. 1, 2002, wherein a liner pin is locked into the distal end of the hard socket (see FIG. 4). In the '876 Perkins distal lock device, a spring biases a plunger and an air-seal o-ring outward unless the wearer/assistant pushes the plunger radially inward.

Advanced, multiple-layer, roll-on liners (also called "second generation" liners) work in combination with the above advanced suspension methods. These liners comprise both a gel layer that lies against the skin to grip the residual limb, and a fabric layer contacts the hard socket but that does not seal against the socket as completely as a gel-only liner. These modern roll-on liners may be connected to the hard socket by proximal attachment systems and/or distal lock mechanisms, and/or may be urged/caused to remain in the hard socket by pressure differential between the well of the hard socket (below the limb) and the ambient atmosphere, hence, the use of the terms "suction" and "vacuum". See the discussion of suction liners in Janusson, et al. (U.S. Pat. No. 6,706,364) and Janusson, et al. (U.S. Pat. No. 6,626,952).

Suction suspensions (more accurately described as "partial suction", as discussed below) for modern roll-on liners typically utilize a pressure inside the distal end of the well of the hard socket that is on average moderately lower than ambient. Because the fabric layer does not provide a complete/absolute seal against the socket, some air leaks into the socket well typically from the top of the socket along the length of the liner. Suction suspensions typically do not utilize any pump or other mechanical device to pump air out of the well of the hard socket. Instead, for example, they utilize the force of the limb pressing into the socket combined with a one-way air expulsion valve adapted to open at a socket well pressure slightly above atmospheric, thus, lowering pressure inside the well to close to ambient pressure. Then, in the swing portion of the gait, the socket "tries" to pull away from the limb due to centrifugal forces, further lowering the pressure in the well to below atmospheric, thus establishing the "suction" condition in the socket. Therefore, in suction suspensions utilizing a multiple-layer liner, the socket well pressure may cycle slightly up above ambient pressure during at least some weight-bearing portions of the wearer's gait, but averages moderately below ambient, for example, in the range of ½-4.9 psi (and preferably 1-1.5 psi) lower than ambient. Such "partial suction" suspensions are more comfortable for many wearers than the "true suction fit" obtained with a gel-only liner.

"Vacuum" systems, on the other hand, utilize a vacuum pump or other mechanical device to remove air from the well, and may establish an air pressure inside the well in the range of about 1 psi below ambient to a much lower pressure approaching 14.7 psi below ambient. More typically, however, vacuum systems operate in a well pressure range lower than suction/partial-suction systems, for example at least 5 psi below ambient and even so low as to approach 14.7 psi below ambient.

In summary, therefore, a suction suspension (especially "partial suction") is typically established and maintained by exhausting air from the distal end of the well when the user dons the socket and during each weight-bearing portion of the user's gait. Vacuum, on the other hand, is typically established and maintained by use of a vacuum pump connected to the well of the hard socket. Both suction and vacuum suspensions, however, typically are supplemented by mechanical connections between the limb liner and the socket, for example, distal locks that engage a protrusion/pin anchored to the distal end of a limb liner.

There is still a need for improved suspension systems for external prostheses, for example, improved mechanical devices that mechanically connect the limb liner to the socket and/or that help optimize control of pressure in the socket well. This is a need, for example, for improved distal lock systems that are easy to use and reliable. There is a need for an improved lock actuation system that is easy and reliable to use with one hand or one finger, which may be used on or with a variety of prostheses including those for legs and arms, and which may be adapted for vacuum, suction, or other attachment systems. Embodiments of the invention meet some or all these needs.

SUMMARY OF THE INVENTION

The invention comprises a lever-actuation system for operating a mechanism on or associated with a limb prosthesis, such as a leg or arm prosthesis. Certain embodiments of the lever-actuation system may be used to manually move a shaft, stem, or other member that is used for mechanical engagement/capture of another portion of the prosthesis and/or limb liner. Certain embodiments may be adapted for opening/closing an air passageway, for example, of a mechanical lock and/or a pressure control system. For example, certain embodiments of the lever actuation system may be used to manually move a portion of a lock for connecting a limb liner to a hard socket. Additionally or alternatively, the lever actuation system may be used to manually move a portion of a valve or other sealing means that controls pressure and/or air flow into or out of a portion of the prosthesis, for example, the well inside the socket that is distal relative to the limb.

The preferred lever-actuation system comprises a lever and can system wherein swinging of the lever causes engagement/movement of the cam to move a shaft, stem, or other member. The cam provides surface(s) that allows the lever, and hence the shaft/stem/member, to stay in the actuated configuration without the user maintaining his hand/fingers on the lever. Said movement of the shaft, stem or other member either locks/unlocks two portions of a prosthesis/liner assembly to/from either other, or opens/closes a passageway, conduit, or other volume for receiving or allowing flow of gas.

Various lever systems may be used in certain embodiments, for example, any first, second, or third class lever. In general, the lever may be described as pivoting/swinging on a fulcrum structure of the prostheses device or of the lock or valve, and said shaft/stein/member being connected to a portion of the lever, pushed and/or pulled by a portion of the lever and therefore moving with or in response to the lever. Thus, the lever swinging/pivoting may cause a linear motion of the shaft/stem/member to slide into or out of a space, to disengage another structure or to open a passageway/conduit, and/or to otherwise affect a structural/configuration change needed for operation of the prosthesis mechanism.

The lever and cam system preferably is adapted so that, most of the time, the lever lies generally flat against the prosthesis or in other non-protruding orientation. This way, during normal use, the lever does not protrude to be accidentally caught or moved by surrounding clothing or objects, and it does not interfere with normal motion or sitting by the user. On the other hand, when the lever is needed to perform the actuation function, the lever may be swung outward into a relatively more-protruding position, where it will remain hands-free (without being held by the user). Therefore, the lever protrudes significantly from the prosthesis during actuating into, or maintaining, the unlatched configuration, but otherwise remains in an unobtrusive and generally non-protruding orientation.

The preferred distal lock comprises a lever-and-cam mechanism that requires the user/assistant to flip/swing a lever, in the form of a latch handle, from a latched position to an unlatched position. The swinging of the lever moves a cammed end of the lever along a portion of the lock housing and causes the connection point of the lever to the shaft of the lock to move outward, which pulls the shaft/stem/member outward as well. This outward movement of the shaft/stein/member, typically longitudinal sliding movement, is the movement that performs the needed function of disengaging the shaft/stem/member to unlock the lock and/or to open an air passageway.

Said flipping/swinging requires little strength and little agility, and so it is convenient and comfortable even if the wearer must bend over to do it. This convenient and comfortable unlatching may be compared to the more difficult radial pushing or pulling of a shaft, for example, the radial pushing of a shaft/plunger such as required in distal locks such as the U.S. Pat. No. 6,334,876 device (FIG. 4). Therefore, especially-preferred distal locks for prostheses use the lever-and-cam system as a portion of a latch/unlatching system that is comfortable and convenient for the wearer, wherein swinging a latch handle unlatches the liner from the lock and/or opens an air passageway, without any need for the user to grasp and push or pull a plunger or shaft.

These objects and features are included in certain embodiments of the invented lever-actuation system for external prostheses, and other objects and features will be apparent to one of skill in the art after reading and viewing this disclosure. While specific structures, means, and methods are shown in the Detailed Description and the Drawings, alternative embodiments are within the broad scope of the invention as defined by the broad statements in the Summary and elsewhere in this document.

BRIEF DESCRIPTION OF THE DRAWINGS

FIGS. 5 and 6 are a top perspective view, and a top view, respectively, of one embodiment of an invented vacuum-version distal lock.

FIG. 7A is a side-cross-sectional view of the vacuum distal lock of FIGS. 5 and 6, showing the lock in the latched (engaged) position, viewed along the line 7A-7A in FIG. 6.

FIG. 7B is a top perspective view of the vacuum distal lock of FIGS. 5-7A, shown with the cammed latch handle swung approximately 90 degrees (from the position in FIGS. 6 and 7A, to a radially-extending position), which actuates unlatching of the lock by pulling the lock's shaft outward.

FIG. 7C is a side-cross-sectional view of the vacuum distal lock of FIG. 7B, with the distal lock in the unlatched position. The cammed ends of the handle may be seen pressing/abutting against the lock body with the lock shaft pulled outward from the axial bore of the lock and the liner pin.

FIGS. 8A-C are various views of the vacuum distal lock of FIGS. 5-7C, all shown with the lock latched. FIG. 8A is a side view, FIG. 8B is a front view, and FIG. 8C is a bottom view. In FIGS. 8A and B, the liner pin assembly normally attached to the threaded insert of the roll-on liner is shown installed in the distal lock (without the insert and without the liner, so that the viewer may understand the location of the liner pin in the distal lock.

FIGS. 10 A-E are various views and details of the threaded body of the embodiment of FIGS. 5-8C that attaches to the radial bore of the housing and through which the shaft slides. FIG. 10A is a perspective view, FIG. 10B is a side view, FIG. 10C is a rear view, FIG. 10D is a front view, and FIG. 10E is a cross-sectional view along the line 10E-10E in FIG. 10D, of the threaded body.

FIGS. 11A-H are various views and details of the lever/latch handle with cammed ends, of the embodiment of FIGS. 5-8C. FIG. 11A is a front-top perspective view. From the perspective of the position of the handle in FIG. 11A, FIGS. 11B-H are, respectively, a top-rear perspective view, a right edge view, a top view, a front view, a bottom view, a left side edge view, and a cross-sectional view along the line 11H-11H in FIG. 11G.

FIG. 12A-E are various views and details of the outer portion of the shaft assembly of the embodiment of FIGS. 5-8C. FIG. 12A is a perspective view, FIG. 12B is a front end view, FIG. 12C is a side view, FIG. 12D is a top view, and FIG. 12E is a cross-sectional view along 12E-12E in FIG. 12D.

FIGS. 13A-G are various views and details of the lock blade of the embodiment of FIGS. 5-8C, also called the "innermost shaft portion" due to this blade being the innermost portion of the shaft assembly that slides in the radial bore and being connected with spring-bias to the outer shaft of FIGS. 12A-E. This blade/innermost-shaft engages the liner pin when the distal lock is in the latched position.

FIG. 14 is perspective view of an alternative shaft assembly that is a one-piece shaft assembly, which may be used in an alternative lever-actuated lock, for example, for a distal lock in applications not requiring that vacuum be maintained in the well of the hard socket.

FIG. 15 is a side view of the shaft of FIG. 14, wherein the innermost end of the shaft (as it would be installed in a lock housing) is at the left.

FIG. 16 is a top view of the shaft of FIGS. 14 and 15.

FIG. 17 is an end view of the shaft of FIGS. 14-16, looking at the innermost end.

DETAILED DESCRIPTION OF CERTAIN EMBODIMENTS

Figures 1, 3:
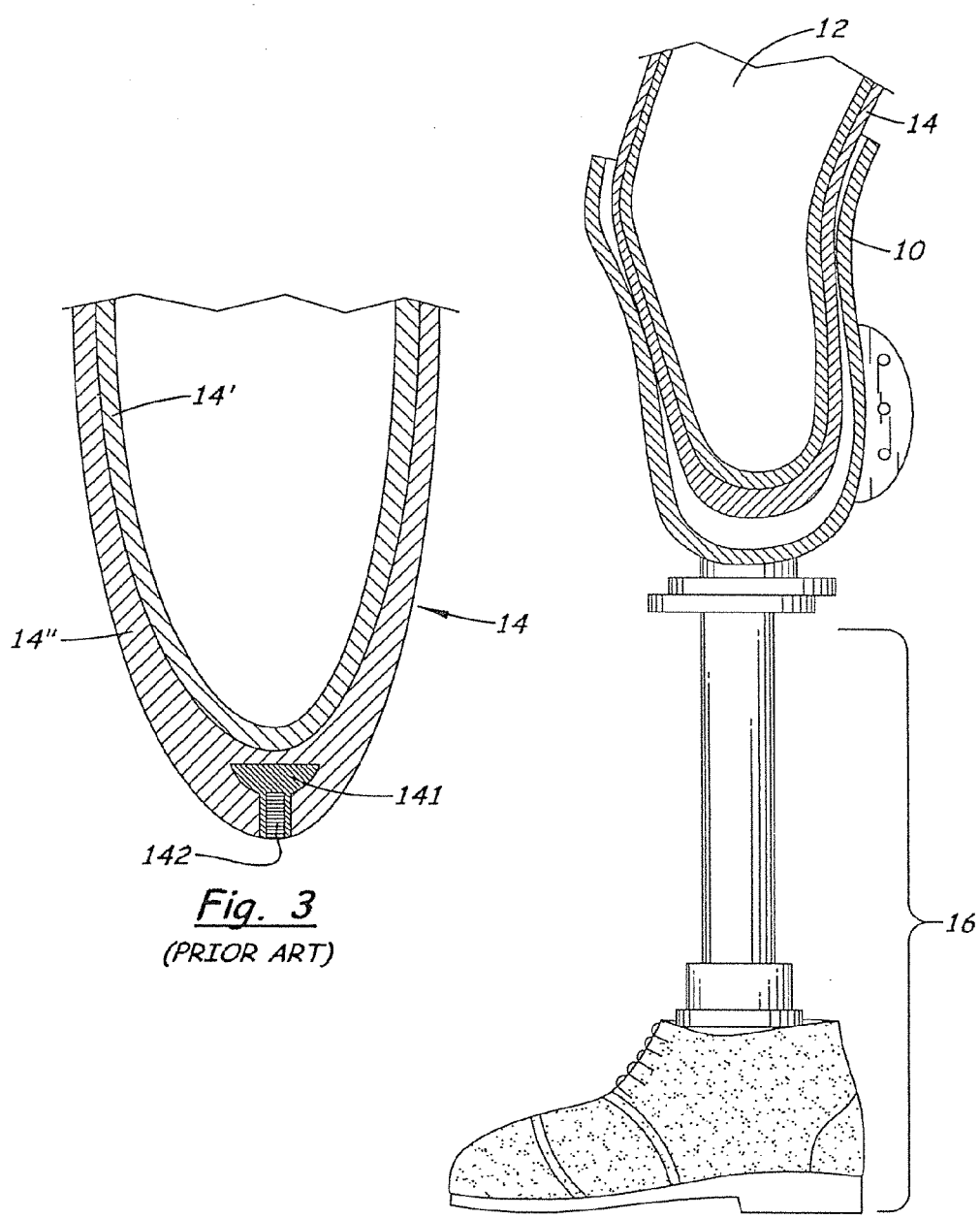
FIG. 1 is a side view of an example of a prior art leg prosthesis, wherein a residual limb wearing a multiple-layer roll-on liner is inserted into the hard socket, and wherein the prosthesis does not include a distal lock and the liner does not comprise a liner pin for cooperation with a distal lock.
FIG. 3 illustrates in cross-section an example roll-on liner that could be used with a liner pin and the distal lock of FIG. 2, wherein the threaded fitting secured in the distal end of the liner would connect to the liner pin.

Using differential air pressure, such as the "suction" or "vacuum" conditions, assists in retaining or suspending a prosthetic limb on a patient's residual limb. "Suction" or "vacuum" suspension typically involves a hard socket and a cooperating liner positioned between the residual limb and the prosthetic socket. Many modern hard sockets are intended to fit accurately and snugly to the residual limb, and they are often "molded" to the shape of the limb. This fit tends to create a close fit between the outer surface of the liner and the inner surface of the hard socket, in effect, sealing or partially-sealing the liner to said inner surface all around the circumference of the residual limb along a significant length of the residual limb. Donning the hard socket, therefore, involves inserting the limb and liner into the socket and releasing pressure that builds in the distal end of the socket well because the air inside the socket does not easily escape past the liner and out of the socket. This release may be accomplished by a hand-operated or automatic valve, vacuum pump, and/or other pressure release/control means. Because of the close-molded fit of many hard sockets to the residual limb of today's wearers, a "suction" or "vacuum" suspension may be possible whether the wearer uses a "first generation" liner that has gel-like inner and outer surfaces, or a "second generation" liner that has a gel-like inner surface and a fabric outer surface, as further discussed below.

Socket liners frequently have been called "suction liners," "gel liners," "roll-on liners" or "suspension liners" and include the "first generation" of gel-layer-only liners, and also the modern "second generation" of multi-layer liners that include an outer layer of fabric and that currently are preferred by most wearers of prosthetics. Socket liners are usually fabricated from silicone, urethane, or other gel-like material that grips the limb to such an extent that they need to be rolled-onto the limb from a rolled-up "doughnut" form, rather than pulled on like a sock. When rolled-on, there is little, if any, air remaining between the inner surface of the roll-on liner and the limb, and the roll-on liner is snug against the limb all the way around the circumference of the limb. Also, the inner surface of the roll-on liner is of such material and tacky texture that air will not be able to, or be very unlikely to, enter between the roll-on liner and limb. Thus, the roll-on liner may be said to form a suction fit and/or a slight compression fit with the limb. A distal force on the liner, such as caused by the swing of a gait with a prosthetic leg, may tug on the roll-on liner but typically does not loosen, lower, or remove the liner from the limb. The liner is difficult to remove except by rolling the top edge of the liner down off of the limb. Thus, longitudinal (axial) forces on the liner do not easily pull the liner out of place or off of the limb. The liners are therefore quite effective in their adhering and staying on the residual limb, and many of the other features of modern suspension systems therefore focus on connection of the hard socket to the liner, as is discussed later in this document.

First generation liners, which featured a gel layer contacting both the residual limb (liner's inner surface) and also the socket (liner's outer surface), can be used to create a fairly high amount of pressure differential between the inside of the socket (in the "well" of the socket) and the surrounding ambient air. This could be accomplished by releasing air pressure from the distal end of the socket well, for example, by a manual valve in the socket wall, after which a very good seal between the limb and the liner, and the liner and the hard socket, could be maintained by the gel liner. Modern "second generation" liners, comprising a thin textile/fabric outer layer that is fixed to the gel-like inside layer, are similar to the first generation regarding the connection to the residual limb, but are different regarding the connection/cooperation with the socket. Because the outer fabric layer of the second generation liners is not as tacky as a gel layer, these second generation liners do not seal as thoroughly as the first generation liners to the inner surface of the hard socket, resulting in less gripping of the socket by the liner and some small amount (albeit it slow) air flow between the liner and the socket interior surface. However, even with these second generation liners, a "partial suction" suspension is still possible, by using one-way air expulsion valves, for example, and a "vacuum" suspension is still possible by using a vacuum pump.

Thus, second generation liners more accurately may be said to allow only "partial suction" (unless a vacuum pump is employed) because the fabric layer(s) do not form what would be called "true" or "pure" suction with the socket. The terms "suction liner" and "suction socket" are still used by many manufacturers, prosthetic technicians, insurance and medicare/medicaid entities, and wearers of prosthetics. The second generation liners, and the "partial suction" suspension they typically provide, are more comfortable for many wearers than a "true suction fit" that is more likely to be obtained by a gel liner without a fabric layer, wherein a gel-seal is formed by the liner both to the limb and to the socket. When a vacuum suspension is needed, the hard socket may be fit with a vacuum pump and control system.

The terms "suction," "suction-fit," and "suction suspension" herein refer to the general process known well in this field of providing a "roll-on" liner or other "interference" liner that helps keep a socket on a residual limb while creating at least a small amount of blockage/hindrance to air freely moving in and out of the socket well past the residual limb, wherein the air moving is typically due to the action of the limb in the socket. A "vacuum suspension" herein describes suspensions that utilize a vacuum pump or other active mechanical device to actively establish and maintain a lower air pressure in the distal end of the interior well of the hard socket, for example, a pressure that is preferably at least 5 psi lower than ambient pressure, and that may approach 14.7 psi less than ambient air pressure. In another approach, "suction", "suction suspension" or "suction fit" may be defined as suspension/fittings that qualify under the medical code for "suction" and "vacuum", "vacuum suspension" or "vacuum fit" may be defined as suspension/fittings that qualify under the medical code for "vacuum".

Certain, but not necessarily all, embodiments of the invented lever-actuation system are part of a distal lock that connects the distal end of a roll-on liner to the distal end of the well of a hard socket. The preferred embodiments of the distal lock comprise an axial bore in a lock housing that is adapted to be installed and secured in/on the distal end of the hard socket. A radial bore is also provided in the lock housing and intersects the axial bore. The axial bore is open, at its top, to the well of the hard socket, and a liner pin secured to the distal end of a roll-on liner may slide into the axial bore when the wearer dons the socket. A shaft assembly is provided in the radial bore, wherein an inner end of the shaft assembly engages the liner pin in the axial bore and an outer end of the shaft assembly is connected to or otherwise operated by the lever. Preferably, the liner pin has circumferential grooves or other indentations that each may receive the inner end of the shaft assembly depending upon how far the liner-covered limb is inserted into the socket and the axial bore. When the distal lock is in the latched position, the inner end of the shaft assembly protrudes far enough into the axial bore to contact and engage the liner pin by extending into one of said grooves/indentations, thus preventing upward axial movement of the pin relative to the axial bore, the housing, and, hence, the removal of the liner-covered limb from the hard socket.

Another object of certain distal lock embodiments is adaptation that allows the liner pin to be inserted and locked into the distal lock, without the distal lock being unlatched prior to, during, or after the insertion. This is accomplished by the lock shaft assembly and pin being configured to allow one-directional movement of the liner pin in the lock when the lock is latched. This is accomplished by the downwardly-moving liner pin being able to enter the lock and temporarily push at least a portion of the shaft assembly (at least the inner end) out of the way sufficiently for the pin to slide down into the lock to its ultimate position in the lock. The shaft assembly (or portion(s) thereof) is/are biased toward/against the pin, including during this pin insertion, so that, after the limb, liner and pin reach a fully-inserted position relative to the socket and lock, the inner end of the shaft assembly engages the pin and prevents removal of the pin unless the lock is unlatched by swinging the lever.

This insertion-without-unlatching system is preferably provided by the shaft assembly inner end and the pin circumferential grooves each having cooperating slanted surfaces. With the distal lock being in the latched position and the liner pin entering the axial bore, the slanted, lower surfaces of the liner pin groove walls impact the slanted, upper surfaces of the inner end of the shaft assembly, with the interaction of said slanted surfaces creating a force vector in an outward direction parallel to the longitudinal axis of the shaft assembly. Thus, each of the slanted pin surfaces that slides down past the shaft assembly temporarily pushes the shaft assembly (or a portion(s) thereof) away from the axial bore to allow the pin to continue entering the axial bore.

The liner pin will come to a rest inside the axial bore when further downward movement stops due to the limb/liner being fully-inserted into the socket. When the pin comes to a rest in the axial bore, the shaft assembly (or a portion(s) thereof) will "snap" into place, due to the continued inward-bias placed on the pin, and the inner end of the shaft assembly will engage the pin to lock the pin from being withdrawn in the upward direction, that is, opposite from the direction in which it entered. The preferred shaft assembly inner end is not tapered/slanted to any significant extent on its lower surface. This way, pulling the pin up does not push the inner end of the shaft assembly out of the way, and removing the liner pin up out of the lock is therefore not possible until the lock is unlatched by swinging the lever.

"Fully-inserted" means the position that the lined limb will reach in the socket as dictated by the fit of the socket to the lined limb, which position includes some space between the bottom of the well and the distal end of the limb. It is not desirable to have the limb "hit" the bottom of the well, as this may be painful and damaging to the limb. It may be noted that the "fully-inserted" position of the liner/limb may shift slightly during walking/running of the user, for example, by a fraction of an inch up to about an inch. This may happen due to additional force being exerted, during portions of the walking/running gait, to push the liner/limb deeper into the socket. One may note that the above-discussed pin and shaft assembly cooperation will allow the pin to be pushed slightly deeper in the axial bore, without unlatching the lock and without disrupting connection of the liner to the socket.

Certain embodiments of a distal lock are adapted to limit, and more preferably to prevent, air flow through the distal lock mechanism under certain conditions, for example, when the distal lock is in a locked condition. Certain embodiments are called "vacuum distal locks" and limit/prevent air flow through the distal lock into the hard socket when the liner pin is locked in the distal lock. Due to such embodiments not being a source of air-leakage, pressure in the socket well may be controlled more reliably and predictably by pressure-control means such as automatic or manual air valves in air-communication with socket well and/or vacuum pumps, for example. Thus, certain embodiments are particularly beneficial in vacuum suspension systems, wherein pressure inside the well of the hard socket is desired to be at least 5 psi less than ambient air pressure, and more preferably from 5 psi to 14.7 psi less than ambient air pressure. This is because, with such a relatively low pressure inside the hard socket, there is a large driving force that would cause air flow into the hard socket through the distal lock, were it not effectively sealed.

The preferred vacuum distal lock is effectively sealed, however, and in certain embodiments in a way wherein lower pressure inside the socket well actually tends to improve the seal of the distal lock, in effect, by pulling the sliding shaft assembly (or portion(s) thereof) inward toward the pin of the roll-on liner and keeping sealing member(s) against sealing surface(s). With the variable of air flow through the distal lock eliminated by the preferred distal lock structure and operation, prosthetic technicians may focus on pressure/suction control by accurate valves and/or pumps without having to account for leaking through the distal lock.

Another object of the preferred vacuum distal lock is that the lock remains in its latched position, which secures the liner pin to the socket and also blocks air flow into and out of the hard socket, even during the portions of the gait when additional force is exerted on the limb/liner relative to the hard socket. In certain vacuum distal lock embodiments, an innermost portion of the shaft assembly ("blade") that cooperates with and engages the pin, is slidable relative to the outer portion of the shaft assembly, but is biased inward relative to the outer portion of the shaft. The air-seal is provided between the outer portion of the shaft and the lock housing, so the innermost portion can slide outward slightly to allow the pin to slide downward in the axial bore, as discussed above, without the outer portion of the shaft sliding relative to the lock housing. Thus, the innermost portion may move to accommodate downward adjustments in the pin, without the air seal being disrupted or broken. Further, it may be noted that vacuum inside the hard socket tends to seat the air seal more firmly, rather than weakening or dislodging it, because vacuum will tend to pull the shaft assembly inward, which will maintain the air seal.

Referring specifically to the Drawings:

Referring to FIGS. 1-4, there are shown prior art systems for an external leg prosthesis. Referring to FIGS. 5-13, there is shown one, but not the only, embodiment of a mechanism for an external prosthesis that comprises lever-actuation. FIGS. 14-19 show another embodiment of a lock shaft assembly for a distal lock of an external prosthesis. The distal lock of FIGS. 5-13 is especially beneficial for vacuum suspension, as it is adapted to block air flow through the distal lock unless and until the user or another person manually and purposely unlatches the distal lock. The shaft assembly of FIGS. 14-19 is an alternative shaft assembly that may be especially-useful may for suction and/or other types of prosthesis suspension/connection, as desired by the wearer and/or judged optimal by the prosthetic technician, wherein the alternative shaft assembly is not specially-adapted to provide an air-seal.

Figure 2:
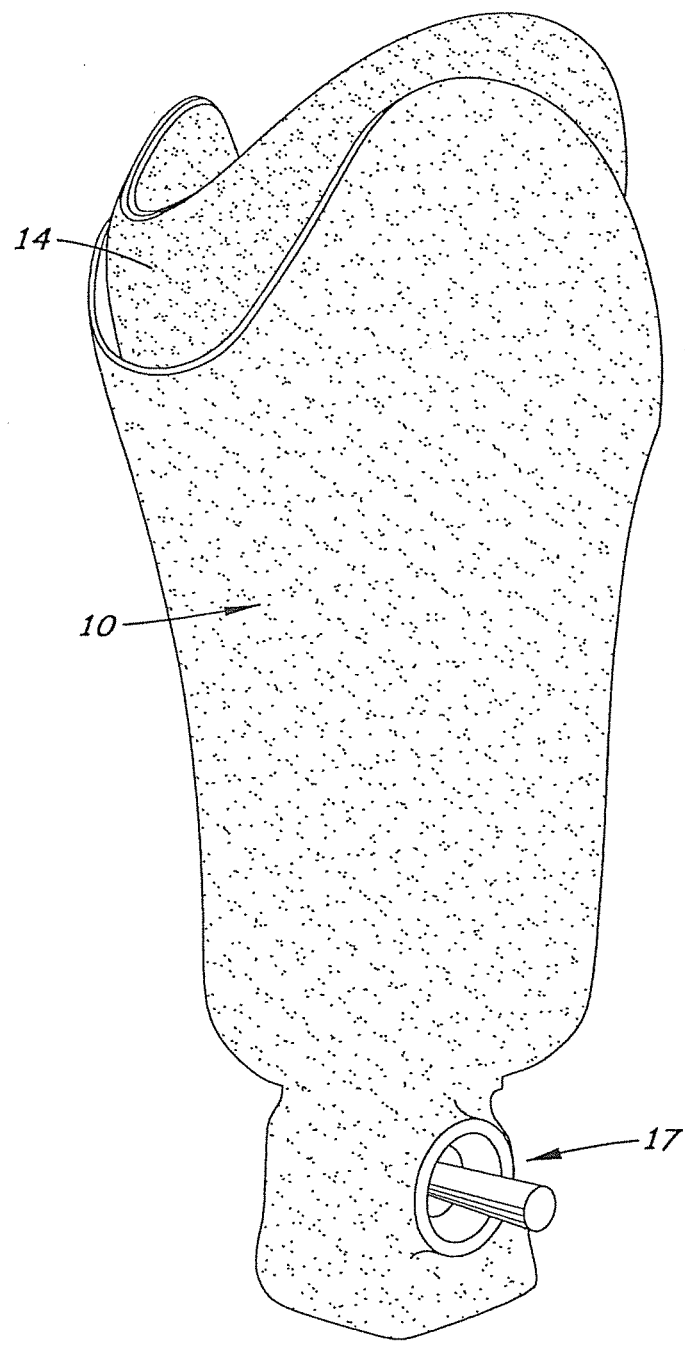
FIG. 2 is an example of a prior art hard socket that includes a distal lock (of the type in Perkins U.S. Pat. No. 6,334,876) incorporated into the distal end of the socket, wherein the plunger/shaft is pushed inward radially to unlatch the distal lock to release a liner pin (not shown in FIG. 2) that is provided at the distal end of the liner received inside the hard socket.

FIG. 1 illustrates schematically a hard socket 10, limb 12 with roll-on liner 14 (preferably with gel layer 14' and fabric layer 14"), and prosthetic foot portion 16. FIGS. 2 and 3 illustrate a prior art prosthesis wherein the liner has a connector for receiving a liner pin (not shown in FIGS. 2 and 3), wherein the liner pin is received and locked into the distal lock 17. In addition to locking to the liner pine, this distal lock is also used to connect the foot portion 16 to the hard socket 10, wherein the distal lock may be molded into, or covered by, portions of the hard socket wall so that it is not visible in detail in/on the finished hard socket. The prior art distal lock 17 portrayed in FIGS. 1-4 is the prior art Perkins lock described above and is not conducive to use in prosthetic systems in which vacuum (typically 5-14.7 psi less than ambient) inside the hard socket well is desirable.

Figure 4:
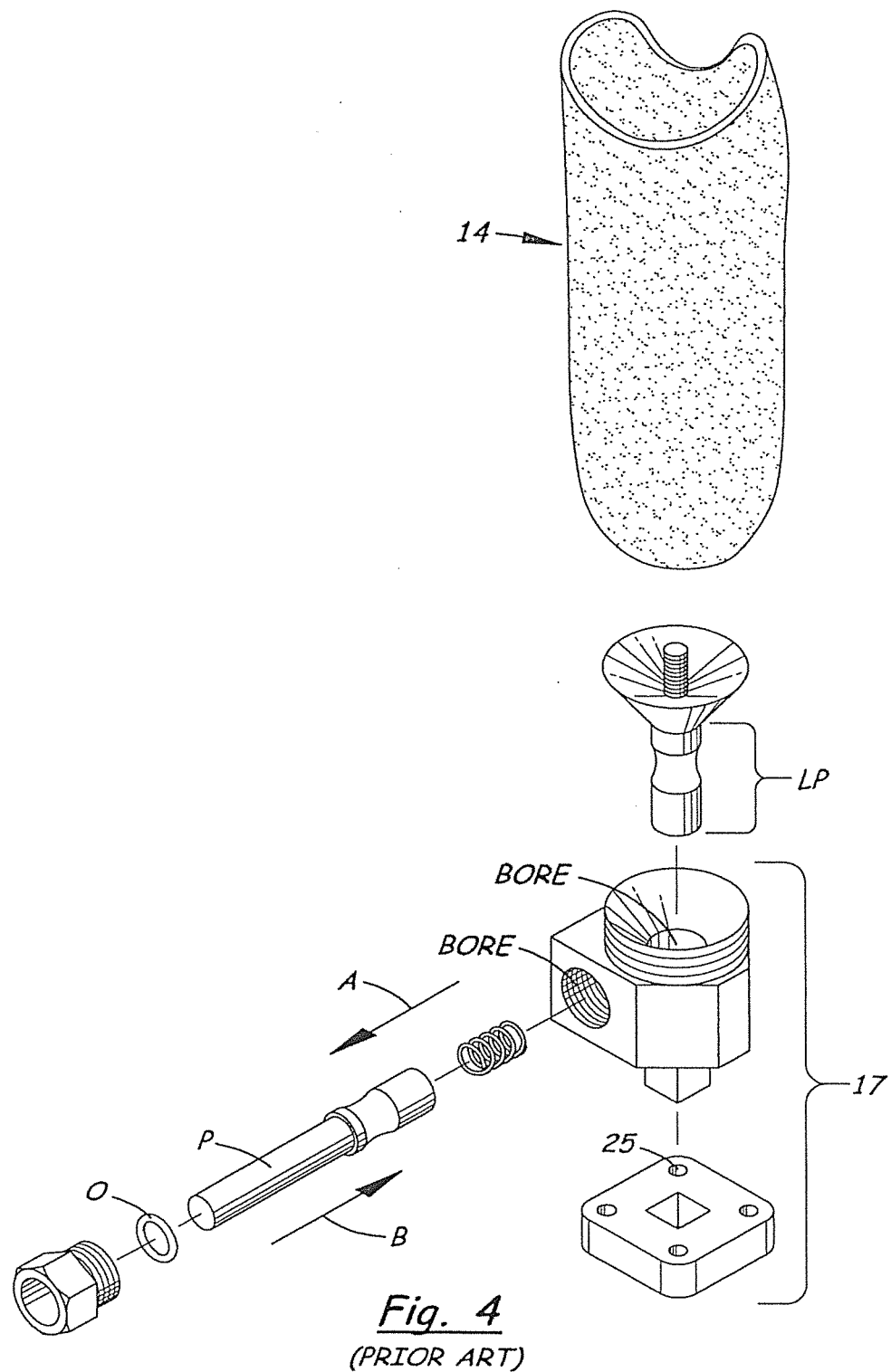
FIG. 4 is an exploded view of a liner, liner pin, and the distal lock of FIG. 2 without the hard socket.
Figure 9A:
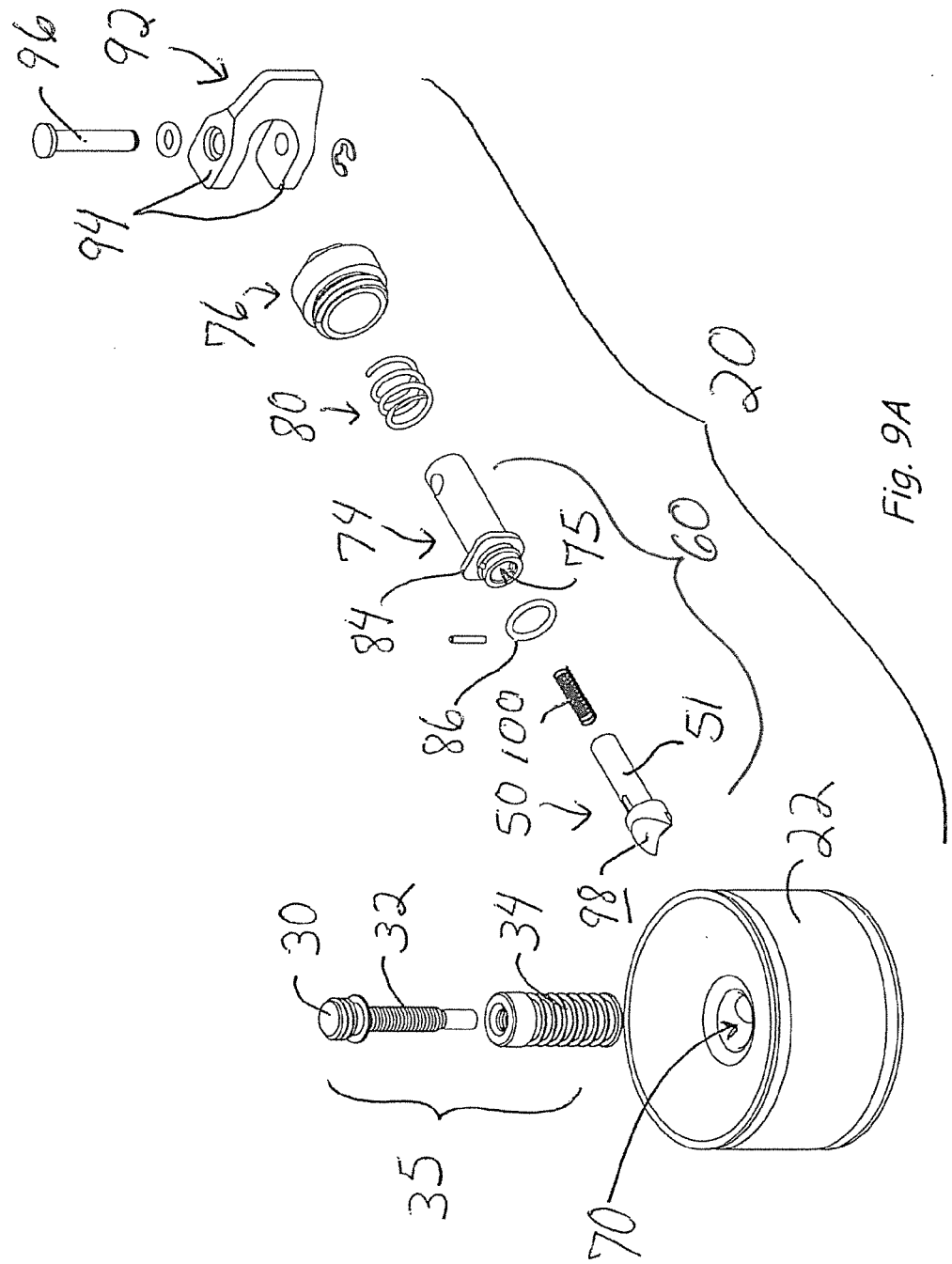
FIGS. 9A and B are exploded views of the embodiment of FIGS. 5-8C, from two perspectives, with the multiple-component liner pin (pin assembly) also shown exploded.
Figure 18:
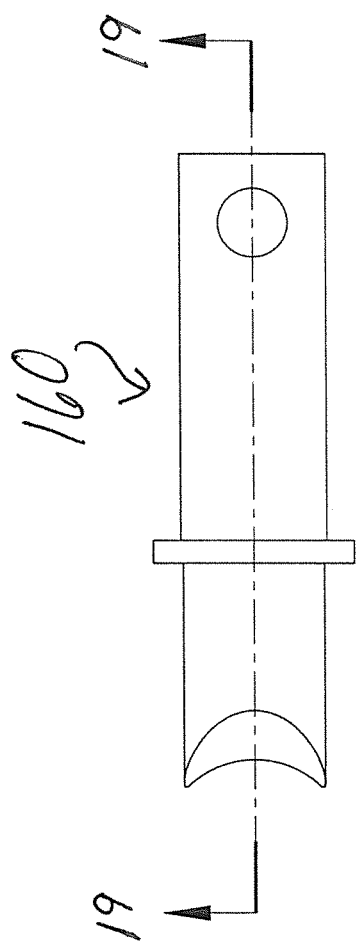
FIG. 18 is a top view of the shaft of FIGS. 14-17.
Figure 19:
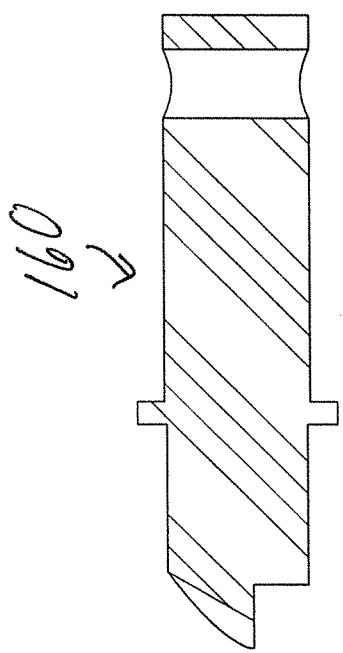
FIG. 19 is a side cross-sectional view of the shaft of FIGS. 14-18, viewed along the line 19-19 in FIG. 18.

One may see in FIG. 3 that piston P slides in direction A due to spring bias, and it is against this spring bias that the wearer/assistant must push the plunger radially inward (direction B) to unlatch the distal lock. If vacuum is established inside the hard socket, the vacuum may cause inward force also in direction B that acts against the bias of the spring and may unseat the o-ring O. This is why this distal lock of FIGS. 2 and 4 is not convenient or operable for prosthetics wherein significant vacuum is desired inside the hard socket; this distal lock, in effect, works against, and substantially prevents, vacuum being established in the hard socket.

In FIGS. 5-13, an improved vacuum distal lock 20, which features one embodiment of a lever-actuation system, is portrayed according to one embodiment of the invention. The distal lock housing 22 houses the main lock mechanism components, is molded into or otherwise connected to the hard socket, and also attaches to the foot portion 16. The upper surface 18 of the distal lock is preferably concave, for example, a conical or other curved shape, for a good fit and/or smooth transition between the surface 18 and the curved distal wall of the hard socket.

Many conventional liners 14 are manufactured with a 10 mm threaded hole at the longitudinal axis of the liner, in the distal end of the liner, as portrayed in the example shown in FIG. 3. Into this threaded hole is installed the threaded head 30 of preferred threaded shaft 32, which in turn is connected by a threaded connection to a larger-diameter pin sleeve 34. This assembly of shaft 32 and sleeve 34 may be considered the preferred pin assembly or "liner pin" 35 (see FIG. 9A). Other liner pin styles and assemblies may be provided and connections between the pin/assembly and the liner other than a threaded connection may be used. The preferred liner pin 35, comprising threaded head 30 on shaft 32 plus sleeve 34, allows the liner pin to be adjustable in length to custom-fit each patient when necessary.

Pin sleeve 34 has multiple circular depressions spaced along its length, wherein each depression results in a protrusion 36 that has a radial top shelf surface 38 perpendicular to the length of the sleeve 34. Each protrusion 36 has a tapered/slanted bottom surface 40, which preferably slants in the range of 45-70 degrees from perpendicular to the length of the sleeve 34. It is these slanted bottom surfaces 40, interacting with the slanted top surface of the blade 50 (the innermost portion of the multiple portion shaft assembly of this embodiment), that allow the sleeve 34 to push the tapered/slanted blade 50 out of the way while it slides down past the blade 50 during entry of the liner pin 35 into the latched lock.

As shown to best advantage in the exploded view of FIG. 9B, axial bore 70 is provided preferably at the central longitudinal axis of the housing 22, and radial bore 72 extends into the housing from the preferably-cylindrical outer side wall. The two bores 70, 72 join at about midway in the housing 22, and it is in this junction that the lock blade 50 engages the sleeve 34 of the liner pin.

Lock blade 50 is provided on the inner end of a radially-extending mechanism, also called the shaft assembly 60, that extends from outside the housing 22 and through the radial bore 72 toward the axial bore 70. The shaft assembly 60 comprises a radial outer shaft portion 74 (hereafter "shaft 74") that slidably extends into the radial bore 72 through threaded body 76. Threaded body 76 connects to a threaded bore opening of the radial bore 72. A main spring 80 resides around shaft 74, with one end abutting an inner flange surface 82 of the body 76 (see FIG. 10E), and the opposite end abutting against the central flange 84 of the radial shaft 74 (see FIGS. 9A and 12E). This serves to bias the radial shaft 74 to slide in the radial bore toward the center of the housing 22, that is, toward the axial bore 70.

An o-ring 86 or other sealing member is provided on the inner surface (facing toward the axial bore 70) of the central flange 84, so that said biasing by the main spring 80 tends to force the o-ring 86 against an inner rim 90 of the radial bore (see FIGS. 7A and C). Thus, whenever the lock is in the "latched" position, the shaft 74 is slid inward to its full extent toward the axial bore. In this latched position, the main spring 80 biases the shaft 74 and o-ring 86 to air-seal the radial bore so that air does not flow past the o-ring and so does not flow from the outside through the radial bore and into the axial bore. Also, in this latched position of the lock, because the spring maintains the o-ring 86 against the inner rim 90, air does not flow out of the axial bore through the radial bore to the outside.

The shaft 74 is sized in length relative to the inner rim 90 and the outer surface of the housing 22, and is connected to a latch handle 92 at its outer end, in such a way that, when the latch handle is in the latched position, the blade 50 extends a short distance into the axial bore 70, and the o-ring 86 seals against the inner rim 90, as shown in FIG. 7A. This is the position wherein the shaft 74 may be said to have "slid inward to its full extend toward the axial bore" and this is the position wherein the handle 92 extends generally circumferentially along and near the outer cylindrical surface of the housing 22.

From the latched condition, the lock may be unlocked or "unlatched" by swinging the lever of the lock, in this embodiment handle 92, to a position wherein it extends radially outward away from the housing 22. See, for example, FIGS. 7B and C, wherein one may see in FIG. 7C that the lever longitudinal axis LA is coaxial with the shaft longitudinal axis SA. The handle 92 comprises a cammed connection to the radial shaft 74. The lever/handle 92 rotates on a pin 96 or other axle, so that the cammed ends 94 impact on and slide along outer flange surface 97 of the threaded body 76. Thus, the fulcrum of lever 92 is the contact point/surface of the cammed ends 94 against flange surface 97 (see FIGS. 10A, B, and E), and the lever pulls the shaft 74 outward against the force of spring 80 by its connection to the shaft 74 by pin 96. By the time the lever/handle 92 is swung about 90 degrees, the generally flat cam surface 95 of each cammed end 94 lies against the generally flat surface 97 and will remain there until the lever/handle is purposefully swung again to force the lever/handle to slide past the roughly 90 degree corner surface 95' of each of the cammed ends.

In this manner, lever/handle 92 may be viewed as a class two lever, wherein the force is applied by the user on the lever/handle end 93, the fulcrum is cammed ends 94 sliding against surface 97 to allow pivoting of the lever, and the load is between lever/handle end 93 and the cammed ends 94. Swinging the handle 92 to the radially-extending position, therefore, forces the radial shaft 74 outward relative to the housing and this outward sliding/translation of the shaft 74 moves the o-ring away from the inner rim 90 of the bore 72 and pulls the blade 50 away from the sleeve 34 and out of the axial bore. This releases the sleeve 34, so that it (and the entire liner pin 35) may be pulled up and out of the axial bore 70 for allowing the liner-covered limb to be removed from the socket. The unsealing of the o-ring allows air flow into the radial bore and from there into the axial bore, which may help lessen vacuum inside the socket and, therefore, may help the wearer remove his/her liner-covered limb from the socket.

It may be understood that in certain embodiments, levers of other classes may be used with associated changes in the housing of the distal valve and/or the connection of the handle to the housing. Further, the inventors prefer a lever as the handle, due to effectiveness and ease of use, but certain embodiments may comprise a handle other than a lever.

The connection of the innermost portion of the shaft to the outer shaft (in this embodiment blade 50 and shaft 74, respectively) is adapted so that the liner pin 35 may be installed in the distal lock even if the distal lock is latched. The blade 50 is slidably connected to the shaft 74, by means of blade end 51 being received in a cavity 75 of the shaft 75, wherein the blade end 51 (and entire blade 50) can slide parallel, and coaxially, relative to the length of the shaft 74. A second spring 100 (see FIGS. 7A, 7C, 9A and B) is provided between the blade end 51, and an interior surface of the cavity 75 of shaft 74 to bias the blade relative to the shaft so that the blade tends to protrude farther from the shaft into the axial bore. Spring 100 is preferably centered along the longitudinal axis of the blade and the shaft by being received in a blade cavity 52, extending out of the cavity 52 to abut against an inner surface 77 of cavity 75. Thus, spring 100 biases surface 53 of the blade cavity 52 away from surface 77 of the shaft cavity 75 (see FIGS. 12E and 13 G). However, when the blade is pushed toward the shaft in the direction of the length of the shaft, the blade will slide to be closer to the shaft, that is, closer to the outer cylindrical surface of the housing. This biased, slidable connection of blade 50 to shaft 74 is further adapted by the blade 50 having a tapered/slanted upper surface 98. Edge 99 is curved on a radius approximately the same as the curvature of the recesses and corresponding protrusions 36 of the sleeve 34. This way, the edge 99, when latched into a recess of the sleeve 34, extends underneath a significant arc of the overhanging protrusion 36 and is not likely to slip relative to the sleeve and is not likely to break. Preferably, edge 99 extends 70-110 degrees along an arc generally centered at the longitudinal axis of the liner pin.

Interaction between the slanted bottom surfaces 40 of the protrusions of the sleeve 34 and the tapered/slanted upper surface 98 of the blade 50 results in the force on the blade by the descending sleeve 34 having a significant radial vector (parallel to the radial bore and the shaft length). If the sleeve is pushed down into the axial bore with the lock latched, the slanted surfaces 40 of the sleeve protrusions 36 push on the tapered/slanted upper surface 98 of the blade, resulting in the blade moving parallel to the radial bore to temporarily be out of the way (outward deeper into the radial bore). After the sleeve 34 is inserted as far as dictated by the fit of the socket to the liner-covered limb (and somewhat depending on the force of the limb into the socket during the user's gait), the sleeve 34 no longer pushes the blade out of the way, and the spring 100 urges the blade to engage the sleeve, and, therefore, to lock the sleeve inside the axial bore. Because of this system, the sleeve may be inserted whether or not the distal lock is latched, and the blade and lock mechanism is not damaged. The user may don the socket without having to unlatch or otherwise manipulate the distal lock.

Also, it may be noted that the slidable connection between the blade 50 and the shaft 74 allows the blade 50 to move out of the way of the protrusions of the liner pin, by sliding outward relative to shaft 74, without breaking the vacuum seal (or "air seal") provided by the shaft's o-ring 86 against surface 90. The blade moves out of the way of the pin assembly 35, while the outer shaft does not move (unless the user purposely unlatches the lock), so vacuum may be maintained inside the well of the socket, during donning, adjustment of the fit of the liner with the socket, and/or during the entire gait of the user.

As discussed above in the Related Art and Summary sections, it is desirable that the preferred distal lock prevent air movement through the vacuum distal lock when it is latched. Lower pressure inside the socket well relative to ambient, for example, as may be established by a vacuum pump connected to the inside of the socket well as will be understood by one of skill in the art. Vacuum inside the well will further tend to keep the distal lock sealed against air flow. This is because vacuum inside the socket will tend to pull the shaft assembly toward the axial bore, pulling the o-ring into tighter sealing engagement against the inner rim of the radial bore. Thus, the distal lock of FIGS. 5-13 is well-adapted for vacuum suspension, and especially for one wherein it is desired to keep a substantial level of vacuum inside the socket, for example, 1-14.7 psi (and more preferably 5-14.7 psi) air pressure lower than ambient.

The main spring 80 is preferably sized and of sufficient strength to maintain the o-ring in sealing position, whenever the distal lock is latched, even if there are pressure fluctuations in the hard socket due to the wearer's gait or for other reasons, and even if the pin assembly 35 moves downward relative to the blade 50 and hence moves the blade outward relative to the shaft. As discussed above, this special spring-biased, slidable blade maintains vacuum during relative motion of the pin assembly 35 and the blade 50 and during relative motion of the blade 50 and the shaft 74. In other words, the preferred vacuum lock device, and the vacuum in the socket, tend to maintain the vacuum condition by maintaining the sliding members of the lock in an inward, sealed condition.

Therefore, certain embodiments of the lever-actuated lock may be described as being for mounting on or in a prosthetic hard socket for connecting a roll-on liner on a residual limb to the hard socket, the lock system comprising: a housing having a first bore for receiving a pin of a roll-on residual limb liner and a second bore transverse and open to said first bore, the pin being slidable in said first bore and having a plurality of radial recesses; a shaft slidable in said second bore, having a first end extending into the housing and a second end extending out of the housing, and a longitudinal axis between said first end and said second end; a blade unit provided in said second bore and having a first blade end and a second blade end, wherein said blade first end extends into the first bore, and the second blade end is slidably connected to said shaft so that said blade unit slides relative to the shaft in a direction parallel to said longitudinal axis; a blade spring provided between the shaft and the blade unit, so that said blade unit is urged away from the shaft toward the first bore to engage at least one of said plurality of radial recesses of said pin; shaft spring adapted to urge the shaft into an inward lock-closed position, toward the first bore of the housing, wherein a seal provided on said first end of the shaft seals against a sealing surface of the housing when the shaft is in said lock-closed position; and a handle connected to the second end of the shaft and accessible at an outer surface of the housing, wherein said handle is adapted to pull the shaft outwards against the bias of the shaft spring into a lock-open position wherein the seal is moved away from the sealing surface to allow air to flow through the lock; and wherein said slidable connection of the blade unit to the shaft is adapted so that the blade slides outward relative to the shaft when outward force is applied to the blade unit, and the shaft and seal remain in lock-closed position to prevent air flow through the lock. The handle may be a lever pivotally connected to the shaft, and wherein said lever has at least one cammed end that pushes against the housing when the handle is swung to the lock-open position to pull the shaft outward from the housing. The housing may comprise a housing portion that comprises said first bore and said second bore and a threaded body portion that screws into the housing portion and through which the shaft passes for connection to the handle, wherein body portion comprises an outer surface against which the at least one cammed end pushes when the lever is swung to the lock-open position. The blade first end may have a curved edge for engaging said plurality of radial recesses of the pin. The blade first end may have a slanted upper surface against which protrusions of the pin push, when the pin moves downward into the first bore, to push the blade unit outward parallel to said longitudinal axis. The lever preferably swings close to an outside surface of the housing when in the lock-closed position, and swings about 90 degrees to extend out from the housing when in the lock-open position.

Certain other embodiments of the lock system, which are particularly adapted to be beneficial for vacuum suspension, may be described as being for connecting a roll-on liner on a residual limb to a hard socket, and the lock system comprising: a roll-on liner comprising a pin having multiple radial protrusions and recesses between said protrusions; and a lock comprising: a housing having a first bore for receiving the pin and a second bore transverse and open to said first bore, the pin being slidable in said first bore; a shaft slidable in said second bore, having a first end extending into the housing and a second end extending out of the housing, and a longitudinal axis between said first end and said second end; a blade unit provided in said second bore and having a first blade end and a second blade end, wherein said blade first end extends into the first bore, and the second blade end is slidably connected to said shaft so that said blade unit slides relative to the shaft in a direction parallel to said longitudinal axis; a blade spring provided between the shaft and the blade unit, so that said blade unit is urged away from the shaft toward the first bore to engage at least one of said plurality of radial recesses of said pin; a shaft spring adapted to urge the shaft into an inward lock-closed position, toward the first bore of the housing, wherein a seal provided on said first end of the shaft seals against a sealing surface of the housing when the shaft is in said lock-closed position; and a handle connected to the second end of the shaft and accessible at an outer surface of the housing, wherein said handle is adapted to pull the shaft outwards against the bias of the shaft spring into a lock-open position wherein the seal is moved away from the sealing surface to allow air to flow through the lock; and wherein said slidable connection of the blade unit to the shaft is adapted so that the blade slides outward relative to the shaft when outward force is applied to the blade unit by the pin moving downward in the first bore, and the shaft and seal remain in lock-closed position to prevent air flow through the lock.

Certain other embodiments of the lock system, which are particularly adapted to be beneficial for vacuum suspension, may be described as lock system for connecting a roll-on liner on a residual limb to a hard socket, the lock system comprising: a roll-on liner comprising a pin having multiple radial protrusions and recesses between said protrusions; and a lock that receives said pin in a first bore and comprises a second bore perpendicular to the first bore, wherein the lock further comprises: a shaft and blade unit provided in the second bore and biased inward toward the first bore to a lock-closed position, the shaft and blade unit comprising a blade slidably connected to a shaft, wherein the blade and shaft are biased away from each other by a blade spring; a seal on the shaft and blade unit adapted to seal against a sealing surface of the second bore when the lock is in the lock-closed position; and a handle connected to the shaft and adapted to pull the shaft outward into a lock-open position wherein the seal is distanced from the sealing surface so that air flows through the lock; wherein, when said pin is pushed downward in the first bore, said protrusions push the blade outward toward the shaft against the bias of the blade spring, and said shaft does not slide outward in the second bore, due to the slidable connection of said blade and shaft, and said seal remains sealed against the sealing surface.

Certain other embodiments of the lock system, which are particularly adapted to be beneficial for vacuum suspension, are described as a lock system for connecting a roll-on liner on a residual limb to a hard socket, the lock system comprising: a roll-on liner comprising a pin; a lock that receives said pin in a first bore and comprises a second bore perpendicular to the first bore, wherein the lock further comprises: a shaft and blade unit provided in the second bore and biased inward toward the first bore to a lock-closed position wherein a seal on the unit seals against a sealing surface of the bore to prevent air flow through the lock and wherein the blade engages the pin to retain the pin in the first bore; a lever handle connected to the shaft and adapted to pull the blade and shaft unit outward from the first bore into a lock-open position wherein the seal is distanced from the sealing surface so that air flows through the lock and the blade disengages from the pin to allow the pin to be removed upward up out of the first bore. The lever handle preferably swings about 90 degrees to move the blade and shaft unit from the lock-closed position to the lock-open position. The blade and shaft unit may be comprised of a blade slidably connected to a shaft slidably, and the lever handle has at least one cammed portion that is pivotally connected to the shaft, wherein, when the lever handle is swung to the lock-open position, the cammed portions push against a surface of a portion of lock housing, to pull the shaft outward from the housing. The blade has an outer end that is received in a longitudinal shaft cavity of the shaft, the blade outer end has a longitudinal blade cavity, and the shaft and blade are biased away from each other by a blade spring received in the blade cavity and pressing against a surface of the shaft cavity. The pin may comprise an inner pin and a pin sleeve that surrounds the inner pin, said pin sleeve having comprising radial protrusions and recesses between the protrusions, wherein said inner pin is threaded for connection to a roll-on liner.

Certain other embodiments of the lock system, which are particularly adapted to be beneficial for vacuum suspension, may be described as comprising: a housing having a first bore at or near a center region of the housing, a second bore that is perpendicular to the first bore, and an elongated sliding unit; the sliding unit comprising an inner blade portion that engages a roll-on liner pin received in the first bore to retain the pin in the first bore, the sliding unit being received in said second bore and biased inward toward the first bore so that the sealing member seals against the second bore to prevent air flow from outside the housing through the second bore and into the first bore (and hence into the hard socket); the lock system further having a handle connected to the sliding member to pull the sliding member outward from the housing to unseal the sealing member and allow air to flow from outside the housing, through the second bore and into the first bore. The handle may be a lever that swings relative to the housing, and said lever having a cammed surface that pushes against the housing to pull the sliding member outward from the housing. The sliding member has an outer portion to which the lever is connected, the inner blade portion is slidably connected to said outer portion, and a spring urges the inner blade portion away from outer portion, and wherein the outer portion and seal remain in place to seal air from flowing into the lock, when the blade portion is forced toward the outer portion by the roll-on liner pin moving downward in the first bore.

Alternative Embodiment of Lever-Actuated Distal Lock

An alternative embodiment of a distal lock and/or lever-actuated mechanism may be provided by modifying the shaft assembly. Alternative shaft assembly 160 in FIGS. 14-19 is less likely to maintain (and in certain embodiment incapable of maintaining) a vacuum inside the hard socket, but may be especially-useful for suction suspension or other prosthesis applications wherein pressure inside the socket well need not be so low. In suction suspensions, wherein an average pressure of about ½-4.9 psi (and preferably 1-1.5 psi) lower than ambient inside the socket well (the bottom of the socket interior, generally below the bottom end of the liner-covered limb) is acceptable most or all of the time, there will not be such a large driving force to cause air flow into the well. Also, in suction suspensions, some of the suction is maintained by purposefully allowing air to be expelled from the socket, with some or all steps, through an auto-expulsion valve on/in the socket. Thus, for suspensions other than vacuum, the distal lock need not maintain a perfect or near-perfect seal.

Alternative shaft assembly 160 may be substituted for shaft assembly 60 in the distal lock 20 of FIGS. 5-13 and operates much like shaft assembly 60 except for a few features described below.

Shaft 160 may have an o-ring or other seal provided on its central flange 184. Or, in view of a perfect/near-perfect seal being unneeded in many applications, the shaft 160 may not have any o-ring or other seal in certain embodiments. In embodiments wherein no o-ring or other seal member is provided, operation of shaft 160 may not (probably will not) seal against the inner rim 90 to seal all/nearly-all air from flowing through the distal lock. No o-ring or other seal is pictured in FIGS. 14-19.

As in shaft assembly 60, shaft 160 is sized in length and is connected to a lever/latch handle 92 at its outer end in such a way that, when the lever/latch handle is in the latched position, the innermost end 150 extends a short distance into the axial bore to engage the liner pin in the lock, as described above and understood from the description of lock 20. This is the position wherein the shaft assembly 160 may be said to have "slid inward to its full extend toward the axial bore" and this is the position wherein the lever/handle 92 extends generally circumferentially along and near the outer cylindrical surface of the housing.

Unlike the slidable connection of blade 50 to shaft 74 in the embodiments of FIGS. 5-13, the shaft assembly of this embodiment is a single unit (shaft 160), and innermost end 150 of shaft 160 does not slide or move relative to the outermost end 174. There is no spring or bias between end 150 and end 174. Therefore, in this simple shaft 160, innermost end 150 is not moveable relative to, and is not biased away from, the opposite, outermost end 174 of the shaft. As the innermost end 150 does not slide relative to the outermost end 174 of the shaft, force that moves innermost end 150 will move the entire shaft 160. When the lock is latched, slanted bottom surfaces of the protrusions of the descending liner pin abut and push against the tapered/slanted upper surface of the innermost end 150 of the shaft 160 to result in the force on the end 150 having a significant radial vector, which moves the entire shaft 160. In this scenarios, the entire shaft 160 to repeatedly move slightly outward, as each protrusion of the liner pin impacts and pushes the innermost end 150 slightly outward. One may note, however, that the protrusions of the liner pin only push on innermost end 150 a fraction of an inch, and so there is only that fraction of an inch movement of the entire shaft assembly (shaft 160). After the liner pin is inserted as far as dictated by the fit of the socket to the liner-covered limb (and somewhat depending on the force of the limb into the socket during the user's gait), the liner pin no longer pushes the innermost end 150 out of the way, and the innermost end 150 stays engaged with the liner pin due to the spring-bias and the lever 92 being in the latched position.

Each time the shaft 160 is pushed outward, as described above (for example, during donning or during a high-force portion of the user's gait that may once or occasionally force the liner pin slightly deeper into the lock), the air passageway between the lock body/housing and the shaft 160 will typically open/increase and air flow through the lock may occur or increase in an outward direction (through the lock to the outside). Further, even when the liner pin is not being pushed to move in the lock, some air flow through the lock may occur (especially if no seal is provided). For example, some air flow outward may occur during the high-force portion of the gait, and some air flow inward may occur the rest of the time (due to suction in the well of the socket below the limb). In suction suspensions utilizing this distal lock, the air flow and pressure in the well of the socket below the limb may be appropriately or adequately controlled by the dimensions of the air passage through the lock, a seal or lack thereof in the lock, and/or other valves provided on the socket (such as auto-expulsion valves). In other words, some air flow may be acceptable and/or desirable in certain embodiments, for various reasons such as those discussed earlier in this document in the Related Art section and/or known to those of skill in the art.

From the latched condition, the lock may be unlocked or "unlatched" by swinging the lever/handle 92 to a position wherein it extends radially outward away from the housing, for example. In this position, as discussed above for lock 20, the generally flat cam surface 95 of each cammed end 94 lies against the generally flat surface 97, and remains in that unlatched position until the lever 92 is purposely swung back to the latched position by a user. Unlatching of the lock holds the innermost end 150 away from the liner pin 35 and frees the liner pin so that user may remove the liner-covered limb from the socket. Also, the little or no resistance to air flow through the lock when it is in the unlatched position, allows air flow into the radial bore and from there into the axial bore, and this will help equilibrate the socket inner pressure with the ambient pressure, to further help the wearer remove his/her liner-covered limb from the socket.

Note that the lever-actuation mechanism, when latched, allows the shaft 160 to be biased against the liner pin 35, but not with so much force that the shaft or its innermost end will be broken. The lever-actuation mechanism, when unlatched, moves the shaft assembly 160 outward. Thus, the user may don the socket without having to unlatch or otherwise manipulate the distal lock, but, if the user wants even less resistance to insertion of the liner pin, he/she may flip the lever partially (about 45 degrees) or fully (about 90 degrees) to move the innermost end 150 out of the way, or nearly out of the way, of the liner pin. If the user flips the lever partially (about 45 degrees), he/she may repeatedly flip it without the lever reaching the point where the lever stays in place in the unlatched position. Then, the user may just release the lever, and it will return to the latched position for use of the prosthesis.

It may be understood, therefore, that the liner pin may be inserted into the distal lock when the lock is latched, as the slidable shaft 160 moves out of the way for the liner pin moving in one direction (inward in the axial bore), and the liner pin may also be inserted into the distal lock when the lock is unlatched, as said unlatching pulls the shaft 160 to a position wherein the innermost end 150 is out of the axial bore.

Figure 20:
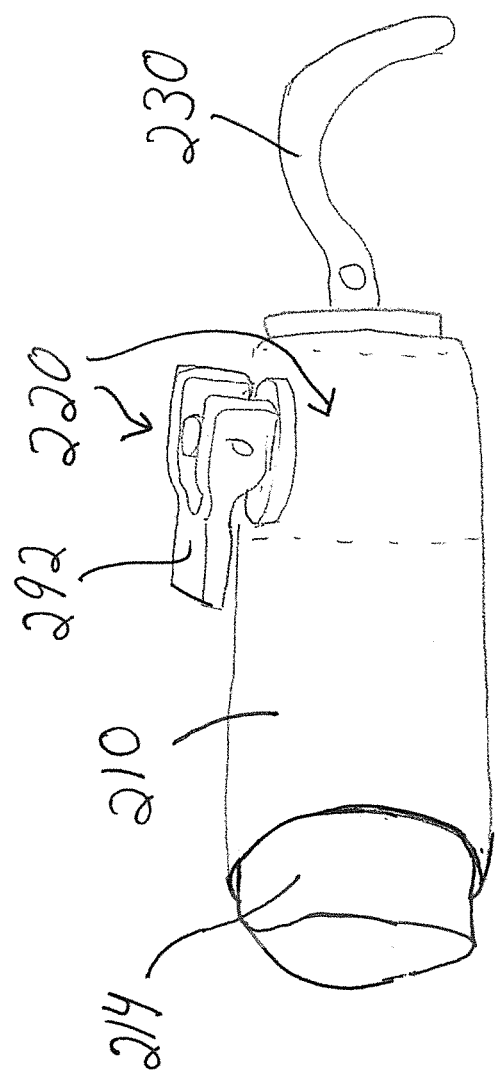
FIG. 20 is a schematic view of an upper extremity prosthetic, for an arm, wherein a lever-actuation system according to certain embodiments of the invention is used for a lock in the distal region of the socket, wherein the proximal edge of a limb liner is shown extending from the open end of the socket. The lever-actuation system in this figure is in the latched position.
Figure 21:
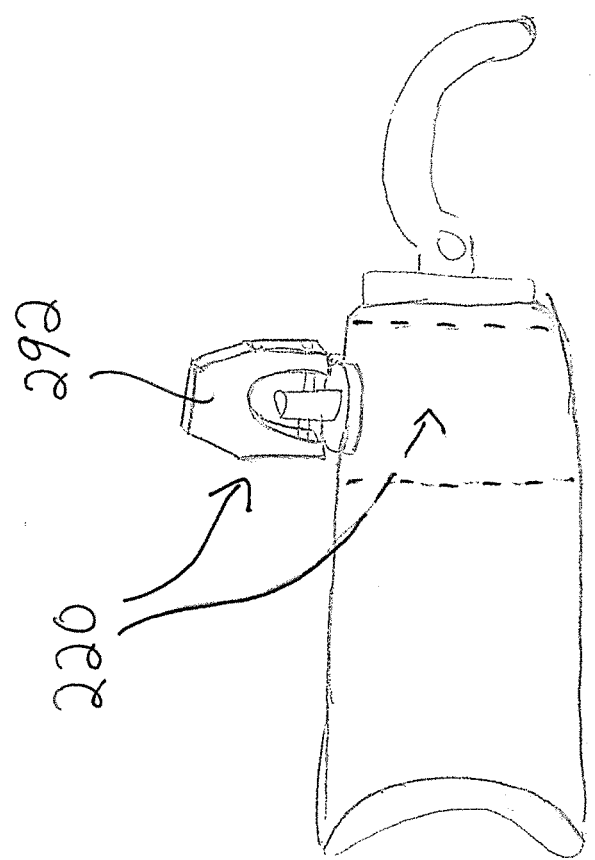
FIG. 21 is a schematic view of an upper extremity prosthetic of FIG. 20, wherein the lever-actuation system has been swung to the unlatched position, for removal of the liner-covered limb.

In FIGS. 20 and 21 is shown an alternative use of a lock embodiment that includes a lever-actuated system. This alternative use comprises a lock 220 provided in the distal region of an arm prosthesis socket 210, wherein the lock 220 receives a "ratchet" pin (similar to pin 35 or another design), a "ratchet" strap, or other member, for example, of an arm liner 214. In a similar manner as discussed above, it may be understood from FIGS. 20 and 21, that the lever 292 can be used to unlatch the lock 220, to free and/or allow adjustment of a pin, strap, or other member on the arm liner. Or, as also discussed above, a "ratchet" effect provided by a liner pin (having circumferential grooves) or other ratcheted member cooperating with a slanted/tapered innermost end of a lock shaft, may allow insertion (but not removal) of the liner-covered limb without unlatching the lock.

In the embodiment of FIGS. 20 and 21, the lock is provided in a distal region of the arm prosthesis socket 210, with the portion hidden/covered by the socket material shown in dashed lines. The hand prosthesis (here, a hook mechanism 230) extends distally from the socket.

Certain embodiments may be described as a locking system actuated by a lever for a prosthetic leg or arm hard socket, the locking system comprising: a limb liner for installation on a residual limb, the limb liner having a liner pin; a lock comprising a housing for connection to a hard socket, the housing having an axial bore at or near a central axis of the housing, and a radial bore; a lock shaft slidable in the radial bore and having an inner end, the lock shaft being biased to a position wherein the inner end extends into the axial bore and engages the liner pin when the liner pin in inserted into the axial bore, so that the liner pin slides in the axial bore in a direction down, but not up, relative to the inner end; and a lever handle connected to an outer end of the lock shaft and adapted to swing to an unlatched position that pulls the lock shaft outward so that said inner end is distanced from the pin. In certain embodiments, the lock shaft is a single piece wherein outward force on the inner end pushes the entire lock shaft radially outward away from the central axis against the bias. The pin may comprise multiple circumferential protrusions, and said inner end may comprise a slanted surface that ratchet-engages with the protrusions as the pin slides down in the axial bore. In certain embodiments, for example, wherein the lock shaft is a single unitary piece, the entire lock shaft may slide radially outward as each protrusion places outward force on said slanted surface of the inner end. The bias may be adapted to slide the lock shaft inward to engage a recess in the pin each time a protrusion of the pin slides down past the slanted surface. The slanted surface may have an inner edge that is curved on an arc, for example, wherein said arc is centered on a radius that is on the longitudinal axis of the pin, so that the arc generally matches shape a portion of the outer circumference of the pin. In certain embodiments, the lock shaft comprises an air-seal that seals to the radial bore when the lock shaft is biased to place the inner end in the axial bore, for limiting air flow through the lock. In other embodiments, the lock system comprises no air-seal between the lock shaft and the radial bore. In certain embodiments, the lock shaft inner end is slideable relative to, and is biased away from, the outer end of the lock shaft, so that the inner end moves out of the way of the liner pin during insertion of the liner pin down into the lock, without moving the entire lock shaft. When the lock shaft inner end is slidable relative to, and biased away from the outer (opposite) end of the lock shaft, the lock shaft may comprise an air-seal that seals the lock shaft to the radial bore when the lock shaft is biased to said position wherein the inner end extends into the axial bore, and the air-seal may remain sealed even then the inner end of the lock shaft slides relative to the outer end of the lock shaft. The lever may have a cammed end adapted to slide along a portion of the housing, so that the lever rests in either the latched or unlatched position without a user holding the lever in said latched or unlatched position.

Certain embodiments may be described as a distal lock for an external prosthetic for connecting a pin of a limb liner to a hard socket, the distal lock comprising a housing with an axial bore receiving the pin and a radial bore, a lock shaft that slides in the radial bore to a latched position wherein the lock shaft engages the pin in the axial bore and to an unlatched position wherein the lock shaft is pulled away from the pin in the axial bore, and a lever connected to the outer end of the lock shaft that swings move the lock shaft to the unlatched position. The lever may be connected to the lock shaft at a pivotal-connection point, and the lever may have at least one cammed end that slides along a portion of the housing so that the pivotal connection point of the lever to the lock shaft moves outward to pull the lock shaft outward to the unlatched position. The lock shaft may be biased into the latched position by a spring. The lock/lock shaft may comprise an air-seal member that seals the lock shaft to the bore in the latched position to block air flow through the distal lock. In certain embodiments, the lock shaft may be a multi-component assembly, comprising an inner portion and an outer portion, the inner portion being biased away from the outer portion toward the axial bore, wherein, when the pin moves down in the axial bore, protrusions on the pin push the inner portion toward the outer portion of the lock shaft. In certain embodiments of the multi-component shaft assembly, the outer portion of the lock shaft may comprise an air-seal-member that seals to the radial bore when the lock shaft is in the latched position, and that remains sealed to the radial bore when the protrusions push the inner portion toward said outer portion of the lock shaft, for example, as the pin "ratchets" down in the axial bore of the lock. In such cases, the preferred system, often for vacuum suspensions, would have the air-seal-member unseal only when the lock shaft is pulled by the lever to the unlatched position. The air-seal-member could be, for example, an o-ring encircling the lock shaft and adapted to seal against a rim about midway along the length of the radial bore.

Although the invention has been described above with reference to particular means, materials and embodiments, it is to be understood that the invention is not limited to these disclosed particulars, but extends instead to all equivalents within the broad scope of the following claims.

The invention claimed is:

1. A locking system actuated by a lever for a prosthetic leg or arm socket, the locking system comprising:
    a limb liner for installation on a residual limb, the limb liner having a liner pin;
    a lock comprising:
    a housing for connection to a prosthetic socket, the housing having a first end and a second end and an axis between said first end and second end, an axial bore at or near said axis of the housing, and a radial bore;
    a lock shaft slidable in the radial bore and having an outer end that is outside the housing, and an inner end, the lock shaft being biased to a position wherein the inner end extends into the axial bore and engages the liner pin when the liner pin is inserted into the axial bore from said first end, so that the liner pin slides in the axial bore relative to said inner end of the lock shaft toward said second end but not toward said first end; and
    a lever outside the housing having a first end and an opposite second end, wherein the lever comprises a pivotal connection to the outer end of the lock shaft between said first end and said second end, and wherein said second end is adapted so that, when the lever is pivoted relative to the lock shaft at said pivotal connection to an unlatched position, said second end pushes against and slides against an outer surface of the housing to move said pivotal connection outward from the housing to pull the lock shaft outward so that said inner end is distanced from the pin.

2. A system as in claim 1, wherein the lock shaft is a single piece wherein outward force on the inner end pushes the entire lock shaft radially outward away from the axis against the bias.

3. A system as in claim 1, wherein the pin comprises multiple circumferential protrusions, and said inner end comprises a slanted surface that ratchet-engages with the protrusions as the pin slides in the axial bore.

4. A system as in claim 3, wherein the entire lock shall slides radially outward as each protrusion places outward force on said slanted surface of the inner end.

5. A system as in claim 4, wherein said bias slides the lock shaft inward to engage a recess in the pin each time a protrusion of the pin slides past the slanted surface.

6. A system as in claim 5, wherein the slanted surface has an inner edge that is curved on an arc.

7. A system as in claim 6, wherein said recess in the pin has a recess radius, and wherein said arc is centered on a radius that generally matches said recess radius.

8. A system as in claim 1, wherein the lock shaft comprises an air-seal that seals to the radial bore when the lock shaft is biased to place the inner end in the axial bore, for limiting air flow through the lock.

9. A system as in claim 1, wherein the lock system comprises no air-seal between the lock shaft and the radial bore.

10. A system as in claim 1, wherein the lock shaft inner end is slideable relative to, and is biased away from, the outer end of the lock shaft, so that the inner end moves out of the way of the liner pin during insertion of the liner pin into the lock, without moving the entire lock shaft.

11. A system as in claim 10, wherein the lock shaft comprises an air-seal that seals the lock shaft to the radial bore when the lock shaft is biased to said position wherein the inner end extends into the axial bore.

12. A locking system as in claim 1, wherein said lock shaft has a shaft longitudinal axis between said outer end and said inner end of the shaft, and said lever has a lever longitudinal axis extending between said first end and said second end, and, in the unlatched position, said lever longitudinal axis extends radially outward away from the housing and is coaxial with said shaft longitudinal axis.

13. A locking system as in claim 1, wherein said outer surface of the housing is an outer surface of a threaded body that is threadably connected to a main body of the housing.

14. A locking system actuated by a lever for a prosthetic leg or arm socket, the locking system comprising:
    a limb liner for installation on a residual limb, the limb liner having a liner pin;
    a lock comprising:
    a housing for connection to a prosthetic socket, the housing having a first end and a second end and an axis between said first end and second end, an axial bore at or near said axis of the housing, and a radial bore;

a lock shaft slidable in the radial bore and having an inner end, the lock shaft being biased to a position wherein the inner end extends into the axial bore and engages the liner pin when the liner pin is inserted into the axial bore from said first end, so that the liner pin slides in the axial bore relative to said inner end of the lock shaft toward said second end but not toward said first end; and a lever connected to an outer end of the lock shaft and adapted to swing to an unlatched position that pulls the lock shaft outward so that said inner end is distanced from the pin;

wherein the lever has a cammed end adapted to slide along a portion of the housing, so that the lever rests in either the latched or unlatched position without a user holding the lever in said latched or unlatched position.

15. A locking system as in claim 14, wherein said lock shaft has a shaft longitudinal axis between said outer end and said inner end of the shaft, and said lever further has a handle end opposite said cammed end, and a lever longitudinal axis extending between said cammed end and said handle end, and wherein, in the unlatched position, said lever longitudinal axis extends radially outward away from the housing and is coaxial with said shaft longitudinal axis.

16. A locking system as in claim 14, wherein said portion of the housing is a threaded body that is threadably connected to a main body of the housing.

17. A locking system for an external prosthetic, the system comprising a limb liner that comprises a pin for use with a prosthetic socket, and a lock comprising a housing with an axial bore receiving the pin and a radial bore, a lock shaft that slides in the radial bore to a latched position wherein the lock shaft engages the pin in the axial bore and to an unlatched position wherein the lock shaft is pulled away from the pin in the axial bore, and a second-class lever outside the housing, having a first end and a second end, and being connected to an outer end of the lock shaft at a pivotal-connection point between said first and said second end, wherein the first end is accessible to a user, and, when the first end is swung by the user to an unlatched position, the second end pushes against an outer surface of the housing as a fulcrum, so that said pivotal connection moves the lock shaft outward to unlatch the lock.

18. A locking system as in claim 17, wherein the lock shaft is biased into the latched position by a spring.

19. A locking system as in claim 17, comprising an air-seal member that seals the lock shaft to the bore in the latched position to block air flow through the lock.

20. A locking system as in claim 17, wherein the lock shaft comprises an inner portion and an outer portion, the inner portion being biased away from the outer portion toward the axial bore, wherein, when the pin moves down in the axial bore, protrusions on the pin push the inner portion toward the outer portion of the lock shaft.

21. A locking system as in claim 17, wherein said lock shaft has a shaft longitudinal axis between said outer end and said inner end of the shaft, and said lever has a lever longitudinal axis extending between said first end and said second end, and, in the unlatched position, said lever longitudinal axis extends radially outward away from the housing and is coaxial with said shaft longitudinal axis.

22. A locking system as in claim 17, wherein said outer surface of the housing is an outer surface of a threaded body threadably connected to a main body of the housing.

23. A locking system for an external prosthetic, the system comprising a limb liner that comprises a pin for use with a prosthetic socket, and a lock comprising a housing with an axial bore receiving the pin and a radial bore, a lock shaft that slides in the radial bore to a latched position wherein the lock shaft engages the pin in the axial bore and to an unlatched position wherein the lock shaft is pulled away from the pin in the axial bore, and a second-class lever outside the housing, having a first end and a second end, and being connected to an outer end of the lock shaft at a pivotal-connection point between said first and said second end, wherein the first end is accessible to a user, and, when the first end is swung by the user to an unlatched position, the second end pushes against an outer surface of the housing as a fulcrum, so that said pivotal connection moves the lock shaft outward to unlatch the lock, the lever second end comprises at least one cammed end that slides along said outer surface of the housing, and that has a flat surface that rests against the outer surface of the housing when the lever is in the unlatched position, so that the lever rests in the unlatched position without a user holding the lever in said unlatched position.

24. A locking system for an external prosthetic, the system comprising a limb liner that comprises a pin for use with a prosthetic socket, and a lock comprising a housing with an axial bore receiving the pin and a radial bore, a lock shaft that slides in the radial bore to a latched position wherein the lock shaft engages the pin in the axial bore and to an unlatched position wherein the lock shaft is pulled away from the pin in the axial bore, and a lever connected to an outer end of the lock shaft that swings to move the lock shaft to the unlatched position;

wherein the lock shaft comprises an inner portion and an outer portion, the inner portion being biased away from the outer portion toward the axial bore, wherein, when the pin moves down in the axial bore, protrusions on the pin push the inner portion toward the outer portion of the lock shaft;

wherein the outer portion of the lock shaft comprises an air-seal-member that seals to the radial bore when the lock shaft is in the latched position, and that remains sealed to the radial bore when the protrusions push the inner portion toward said outer portion of the lock shaft.

25. A locking system as in claim 24, wherein the air-seal-member unseals only when the lock shaft is pulled by the lever to the unlatched position.

26. A locking system as in claim 25, wherein the air-seal-member is an o-ring encircling the lock shaft and adapted to seal against a rim about midway along the length of the radial bore.

* * * * *